United States Patent [19]

Ashton et al.

[11] Patent Number: 4,493,843

[45] Date of Patent: Jan. 15, 1985

[54] INDOLE AND INDOLINE CARBOXYLIC ACID COMPOUNDS AND METHOD OF USE

[75] Inventors: Michael J. Ashton; Andrew W. Bridge, both of Chelmsford; Robert F. Chapman, Benfleet; Garry Fenton, Romford; Anthony H. Loveless, Hornchurch; David Riddell, Billericay, all of England

[73] Assignee: May & Baker Limited, Essex, England

[21] Appl. No.: 380,838

[22] Filed: May 21, 1982

Related U.S. Application Data

[63] Continuation of Ser. No. 274,211, Jun. 16, 1981, abandoned.

[30] Foreign Application Priority Data

Jun. 18, 1980 [GB] United Kingdom .............. 8019948

[51] Int. Cl.³ .................... C07D 209/12; A61K 31/40
[52] U.S. Cl. ................................. 424/274; 548/490; 548/510
[58] Field of Search ............... 548/490, 510; 424/274

[56] References Cited

U.S. PATENT DOCUMENTS

| | | | |
|---|---|---|---|
| 3,076,814 | 2/1963 | Speeter et al. | 548/490 |
| 3,865,838 | 2/1975 | Popelak et al. | 424/274 |
| 3,901,899 | 8/1975 | Gassman | 548/439 |
| 3,950,343 | 4/1976 | Phillipp et al. | 548/490 |
| 3,992,392 | 11/1976 | Gassman | 548/439 |
| 4,070,470 | 1/1978 | Nakagawa et al. | 424/258 |
| 4,343,811 | 8/1982 | Hurnaus et al. | 424/274 |

OTHER PUBLICATIONS

Z. Esayan et al., Chem. Abstracts, 72:21657W (1970).
Z. Esayan et al., Chem. Abstracts, 70:11476f (1969).
Zh Akopyan et al., Chem. Abstracts, 81:169387q (1974).

*Primary Examiner*—Donald G. Daus
*Assistant Examiner*—S. A. Gibson
*Attorney, Agent, or Firm*—Stevens, Davis, Miller & Mosher

[57] ABSTRACT

Indole and indoline derivatives of the formula:

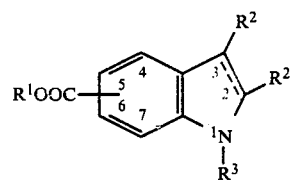

wherein === indicates a double bond or a single bond between carbon atoms, $R^1$ represents hydrogen, alkyl of 1 through 6 carbon atoms, or alkyl of 1 through 6 carbon atoms substituted by one or more than one of the same type of substituents selected from the hydroxy group, alkenyl groups of 2 through 5 carbon atoms, and alkanoyloxy groups of 2 through 7 carbon atoms, and one of the symbols $R^2$ represents alkyl of 6 through 24 carbon atoms and the other symbol $R^2$ represents alkyl of 1 through 24 carbon atoms or hydrogen, and $R^3$ represents alkyl of 1 through 6 carbon atoms or hydrogen, are new compounds possessing useful pharmacological properties. They are of use in the treatment of diabetes mellitus, hyperlipoproteinaemic states, of atherosclerosis, and of associated conditions.

34 Claims, No Drawings

INDOLE AND INDOLINE CARBOXYLIC ACID COMPOUNDS AND METHOD OF USE

This is a continuation of application Ser. No. 274,211 filed June 16, 1981, now abandoned.

DESCRIPTION

This invention relates to new therapeutically useful indole and indoline derivatives, to processes for preparing them, and to pharmaceutical compositions containing them.

The indole and indoline derivatives of the present invention are those compounds of the general formula:

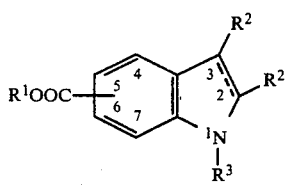

I wherein ---- indicates a double bond or a single bond between carbon atoms, $R^1$ represents a straight- or branched-chain alkyl group containing from 1 to 6 carbon atoms (which may be substituted by one or more than one of the same type of substituents selected from the hydroxy group, alkenyl groups containing from 2 to 5 carbon atoms, e.g. vinyl, and alkanoyloxy groups containing from 2 to 7 carbon atoms, e.g. pivaloyloxy) or, more particularly, a hydrogen atom, and one of the symbols $R^2$ represents a straight- or branched-chain alkyl group containing from 6 to 24, preferably from 7 to 20, carbon atoms and the other symbol $R^2$ represents a straight- or branched-chain alkyl group containing from 1 to 24 carbon atoms (preferably a straight- or branched-chain alkyl group containing from 1 to 6 carbon atoms) or preferably a hydrogen atom, and $R^3$ represents a straight- or branched-chain alkyl group containing from 1 to 6 carbon atoms or preferably a hydrogen atom, and pharmaceutically acceptable salts thereof.

When $R^1$ is an alkyl or substituted alkyl group it may be, for example, a methyl, ethyl, butyl, 2,3-dihydroxyprop-1-yl, allyl or pivaloyloxymethyl group.

The group $R^1OOC$ is attached to the 4 or 7 or, preferably, the 5 or 6 position of the indole or indoline ring system.

When one of the symbols $R^2$ represents a hydrogen atom or a straight- or branched-chain alkyl group containing from 1 to 5 carbon atoms (preferably the methyl group) it is preferably attached to the 3 position of the indole or indoline ring system.

Preferred indole or indoline derivatives of the present invention are those compounds of the general formula:

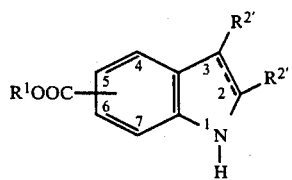

II wherein ---- indicates a double bond or a single bond between carbon atoms, $R^1$ represents a straight- or branched-chain alkyl group containing from 1 to 6 carbon atoms (e.g. methyl, ethyl or butyl) or, more particularly, a hydrogen atom, and one of the symbols $R^{2'}$ represents a straight- or branched-chain alkyl group containing from 6 to 24, preferably 7 to 20, carbon atoms and the other symbol $R^{2'}$ represents a straight- or branched-chain alkyl group containing from 1 to 24 carbon atoms (preferably, when it represents an alkyl group containing from 1 to 5 carbon atoms it is attached to the 3 position of the indole or indoline ring system) and pharmaceutically acceptable salts thereof.

Other preferred indole or indoline derivatives of the present invention are those compounds of the general formula:

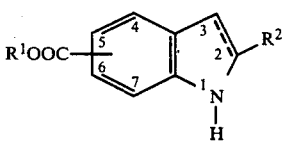

III wherein ---- indicates a double bond or a single bond between carbon atoms, $R^1$ represents a straight- or branched-chain alkyl group containing from 1 to 6 carbon atoms (e.g. methyl, ethyl or butyl) or, more particularly, a hydrogen atom, and $R^2$ represents a straight- or branched-chain alkyl group, containing from 6 to 24, preferably from 7 to 20, carbon atoms, and pharmaceutically acceptable salts thereof.

The group $R^1OOC-$ depicted in general formulae II and III is attached to the 5 or 6 position of the indole or indoline ring system.

It will be understood by those skilled in the art that when ---- represents a single bond between carbon atoms and one of the symbols $R^2$ represents a hydrogen atom the compounds of general formula I may exist in optically isomeric forms. It will be further understood by those skilled in the art that when the symbol ---- represents a single bond between carbon atoms and both of the symbols $R^2$ represent alkyl groups the compounds of general formula I may exist in optically isomeric forms and also as diastereoisomers. Furthermore, in certain cases the substituents $R^1$, $R^2$ and $R^3$ contribute to optical isomerism. All such forms are embraced by the present invention.

By the term "pharmaceutically acceptable salt" in relation to compounds of general formula I is meant a salt formed by reaction with an acid when ---- indicates a single bond between carbon atoms or, when $R^1$ represents a hydrogen atom, by reaction with a base, so that the anion (in the case of an acid addition salt) or the cation (in the case of a salt formed by a compound of general formula I wherein $R^1$ represents a hydrogen atom) is relatively innocuous to the animal organism when used in therapeutic doses so that the beneficial pharmacological properties of the parent compound of general formula I are not vitiated by side-effects ascribable to the said anion or cation.

Suitable acid addition salts include salts derived from inorganic acids, for example hydrochlorides, hydrobromides, phosphates, sulphates and nitrates, and organic salts, for example methanesulphonates, 2-hydroxyethanesulphonates, oxalates, lactates, tartrates, acetates, salicylates, citrates, propionates, succinates, fumarates, maleates, methylene-bis-β-hydroxynaphthoates, gentisates and di-p-toluoyltartrates.

Suitable salts formed by compounds of general formula I wherein $R^1$ represents a hydrogen atom include the alkali metal (e.g. sodium and potassium), alkaline earth metal (e.g. calcium and magnesium), and ammonium salts, and salts of amines known in the art to be pharmaceutically acceptable, e.g. ethylene diamine, choline, diethanolamine, triethanolamine, octadecylamine, diethylamine, triethylamine, 2-amino-2-(hydroxymethyl)propane-1,3-diol and 1-(3,4-dihydroxyphenyl)-2-isopropylaminoethanol.

It is to be understood that, where in this specification reference is made to compounds of general formula I, it is intended to refer also to their pharmaceutically acceptable salts as indicated above, where the context so permits.

The compounds of general formula I possess useful pharmacological properties, in particular hypolipidaemic activity, and some are intermediates for the preparation of the other therapeutically useful derivatives. For example, they lower the concentrations of cholesterol and of triglycerides in the blood. Furthermore they reduce the proliferation of arterial smooth muscle cells which is a major feature of atheromatous plaques. The compounds of general formula I also lower blood glucose levels in mice suffering from diabetes mellitus. Thus, they are of utility in the prevention or treatment of diabetes mellitus, hyperlipoproteinaemic states, of atherosclerosis, and of associated conditions such as angina, myocardial infarction, cerebral vascular occlusion, arterial aneurism, peripheral vascular disease, recurrent pancreatitis and xanthomas.

Compounds of general formula I which are of particular interest include the following compounds, their isomeric forms and their salts:

| | |
|---|---|
| 2-(n-tridecyl)indole-6-carboxylic acid | A |
| 2-(n-heptadecyl)indole-6-carboxylic acid | B |
| 2-(n-undecyl)indole-6-carboxylic acid | C |
| 2-(n-pentadecyl)indole-6-carboxylic acid | D |
| 2-(n-heptadecyl)indole-5-carboxylic acid | E |
| 2-(n-undecyl)indole-5-carboxylic acid | F |
| 2-(n-pentadecyl)indole-5-carboxylic acid | G |
| 2-(n-tridecyl)indole-5-carboxylic acid | H |
| 2-(n-pentadecyl)indole-7-carboxylic acid | I |
| 2-(n-pentadecyl)indole-4-carboxylic acid | J |
| (RS)-2-(n-pentadecyl)indoline-6-carboxylic acid | K |
| 2-(n-nonyl)indole-6-carboxylic acid | L |
| 2-(n-decyl)indole-5-carboxylic acid | M |
| 2-(n-decyl)indole-6-carboxylic acid | N |
| 2-(n-nonyl)indole-5-carboxylic acid | O |
| 2-(n-octyl)indole-6-carboxylic acid | P |
| 2-(n-heptyl)indole-5-carboxylic acid | Q |
| 2-(n-heptyl)indole-6-carboxylic acid | R |
| 2-(n-dodecyl)indole-6-carboxylic acid | S |
| 2-(n-octadecyl)indole-5-carboxylic acid | T |
| ethyl 2-(n-undecyl)indole-5-carboxylate | U |
| 2-(n-octadecyl)indole-6-carboxylic acid | V |
| 2-(n-undecyl)indole-4-carboxylic acid | W |
| 2-(n-octyl)indole-5-carboxylic acid | X |
| 2-(n-dodecyl)indole-5-carboxylic acid | Y |
| 2-(n-nonyl)indole-4-carboxylic acid | Z |
| 2-(n-eicosyl)indole-5-carboxylic acid | AA |
| ethyl 2-(n-pentadecyl)indole-5-carboxylate | BB |
| ethyl 2-(n-dodecyl)indole-6-carboxylate | CC |
| ethyl 2-(n-heptyl)indole-5-carboxylate | DD |
| ethyl 2-(n-pentadecyl)indole-4-carboxylate | EE |
| ethyl 2-(n-undecyl)indole-6-carboxylate | FF |
| n-butyl 2-(n-undecyl)indole-6-carboxylate | GG |
| n-butyl 2-(n-pentadecyl)indole-5-carboxylate | HH |
| ethyl 2-(n-dodecyl)indole-5-carboxylate | II |
| methyl 2-(n-undecyl)indole-6-carboxylate | JJ |
| n-butyl 2-(n-dodecyl)indole-5-carboxylate | KK |
| methyl 2-(n-pentadecyl)indole-5-carboxylate | LL |
| n-butyl 2-(n-pentadecyl)indole-4-carboxylate | MM |
| 2-(n-tetradecyl)indole-5-carboxylic acid | NN |
| 2-(n-hexadecyl)indole-5-carboxylic acid | OO |
| 2-(n-nonadecyl)indole-5-carboxylic acid | PP |
| 2-(n-tricosyl)indole-5-carboxylic acid | QQ |
| (RS)-2-(1-methyldecyl)indole-5-carboxylic acid | RR |
| 2-(n-tetradecyl)indole-6-carboxylic acid | SS |
| 2-(n-hexadecyl)indole-6-carboxylic acid | TT |
| 2-(n-eicosyl)indole-6-carboxylic acid | UU |
| (RS)-2-(1-methyldecyl)indole-6-carboxylic acid | VV |
| 2-(n-nonyl)indole-7-carboxylic acid | WW |
| 2-(n-undecyl)indole-7-carboxylic acid | XX |
| (RS)-2-(n-undecyl)indoline-5-carboxylic acid | YY |
| (RS)-2-(n-decyl)indoline-6-carboxylic acid | ZZ |
| (RS)-2-(n-pentadecyl)indoline-5-carboxylic acid | AAA |
| (RS)-2-(n-heptyl)indoline-5-carboxylic acid | ABB |
| (RS)-2-(n-decyl)indoline-5-carboxylic acid | ACC |
| (RS)-2-(n-heptadecyl)indoline-5-carboxylic acid | ADD |
| (RS)-2-(n-heptyl)indoline-6-carboxylic acid | AEE |
| (RS)-2-(n-undecyl)indoline-6-carboxylic acid | AFF |
| (RS)-2-(n-tetradecyl)indoline-6-carboxylic acid | AGG |
| (RS)-ethyl 2-(n-undecyl)indoline-6-carboxylate | AHH |
| methyl 2-(n-neptyl)indole-6-carboxylate | AII |
| ethyl 2-(n-heptyl)indole-6-carboxylate | AJJ |
| n-butyl 2-(n-heptyl)indole-6-carboxylate | AKK |
| n-butyl 2-(n-dodecyl)indole-6-carboxylate | ALL |
| ethyl 2-(n-tridecyl)indole-6-carboxylate | AMM |
| methyl 2-(n-pentadecyl)indole-6-carboxylate | ANN |
| ethyl 2-(n-pentadecyl)indole-6-carboxylate | AOO |
| n-butyl 2-(n-pentadecyl)indole-6-carboxylate | APP |
| n-butyl 2-(n-eicosyl)indole-6-carboxylate | AQQ |
| n-butyl 2-(n-heptyl)indole-5-carboxylate | ARR |
| methyl 2-(n-heptyl)indole-5-carboxylate | ASS |
| methyl 2-(n-undecyl)indole-5-carboxylate | ATT |
| n-butyl 2-(n-undecyl)indole-5-carboxylate | AUU |
| methyl 2-(n-dodecyl)indole-5-carboxylate | AVV |
| methyl 2-(n-heptadecyl)indole-5-carboxylate | AWW |
| (RS)(RS)-2,3-dihydroxyprop-1-yl 2-(n-decyl)-indoline-6-carboxylate | AXX |
| methyl 3-(n-dodecyl)indole-6-carboxylate | AYY |
| methyl 3-(n-octyl)indole-6-carboxylate | AZZ |
| methyl 3-(n-hexadecyl)indole-6-carboxylate | BAA |
| methyl 3-(n-octadecyl)indole-6-carboxylate | BBB |
| methyl 3-(n-hexadecyl)indole-5-carboxylate | BCC |
| 3-(n-dodecyl)indole-6-carboxylic acid | BDD |
| 3-(n-octyl)indole-6-carboxylic acid | BEE |
| 3-(n-hexdecyl)indole-6-carboxylic acid | BFF |
| 3-(n-octadecyl)indole-6-carboxylic acid | BGG |
| 3-(n-hexadecyl)indole-5-carboxylic acid | BHH |
| (RS)-1-methyl-2-(n-undecyl)indoline-6-carboxylic acid | BII |
| (RS)-1-methyl-2-(n-undecyl)indoline-5-carboxylic acid | BJJ |
| (RS)-methyl 3-(n-octadecyl)indoline-5-carboxylate | BKK |
| (RS)-methyl 3-(n-decyl)indoline-5-carboxylate | BLL |
| (RS)-methyl 3-(n-octyl)indoline-5-carboxylate | BMM |
| (RS)-methyl 3-(n-hexadecyl)indoline-5-carboxylate | BNN |
| (RS)-3-(n-octadecyl)indoline-5-carboxylic acid | BOO |
| (RS)-3-(n-decyl)indoline-5-carboxylic acid | BPP |
| (RS)-3-(n-octyl)indoline-5-carboxylic acid | BQQ |
| (RS)-3-(n-hexadecyl)indoline-5-carboxylic acid | BRR |
| 3-(n-octadecyl)indole-5-carboxylic acid | BSS |
| 3-(n-octyl)indole-5-carboxylic acid | BTT |
| (RS)-methyl 3-(n-undecyl)indoline-6-carboxylate | BUU |
| (RS)-methyl 3-(n-decyl)indoline-6-carboxylate | BVV |
| (RS)-methyl 3-(n-pentadecyl)indoline-6-carboxylate | BWW |
| (RS)-3-(n-undecyl)indoline-6-carboxylic acid | BXX |
| (RS)-3-(n-decyl)indoline-6-carboxylic acid | BYY |
| (RS)-3-(n-pentadecyl)indoline-6-carboxylic acid | BZZ |
| (RS)-3-(n-dodecyl)indoline-6-carboxylic acid | CAA |
| (RS)-3-(n-octadecyl)indoline-6-carboxylic acid | CBB |
| (RS)-3-(n-octyl)indoline-6-carboxylic acid | CCC |
| (RS)-3-(n-hexadecyl)indoline-6-carboxylic acid | CDD |
| (RS)-methyl 3-(n-octyl)indoline-6-carboxylate | CEE |
| (RS)-methyl 3-(n-hexadecyl)indoline-6-carboxylate | CFF |
| (RS)-1-methyl-2-(n-tetradecyl)indoline-6-carboxylic acid | CGG |
| 1-methyl-2-(n-undecyl)indole-6-carboxylic acid | CHH |

-continued

| | |
|---|---|
| 1-methyl-2-(n-pentadecyl)indole-5-carboxylic acid | CII |
| (RS)-2-(1-methylheptadecyl)indole-6-carboxylic acid | CJJ |
| (RS)-2-(1-methylheptadecyl)indole-5-carboxylic acid | CKK |
| (RS)(RS)-2-(1-methylhetadecyl)indoline-6-carboxylic acid | CLL |
| (RS)(RS)-2-(1-methylheptadecyl)indoline-5-carboxylic acid | CMM |
| 2(RS),3(RS)-2-(n-undecyl)-3-methylindoline-6-carboxylic acid | CNN |
| 2(RS),3(RS)-2-(n-undecyl)-3-methylindoline-5-carboxylic acid | COO |
| 2-(n-undecyl)-3-methylindole-6-carboxylic acid | CPP |
| 2-(n-undecyl)-3-methylindole-5-carboxylic acid | CQQ |
| (RS)-2-(n-undecyl)indoline-4-carboxylic acid | CRR |
| (RS)-2-(n-eicosyl)indoline-5-carboxylic acid | CSS |
| 2(RS),3(RS)-2-(n-heptyl)-3-methylindoline-6-carboxylic acid | CTT |
| (RS)-2-(1-ethyldecyl)indole-6-carboxylic acid | CUU |
| (RS)-2,3-dihydroxyprop-1-yl 2-(n-undecyl)-indole-6-carboxylate | CVV |

The letters A to CVV are assigned to the compounds for easy reference later in the specification, for example in the following Tables.

The pharmacological properties of the compounds of general formula I or salts thereof were demonstrated in the following tests:

Hypolipidaemic Activity in Rats

Male Wistar rats each weighing between 120 and 150 g were caged in groups of eight and fed a powdered diet for 10 days. For the last 7 days of that period the test compound was administered orally by mixing the compound in the diet and allowing the animals to feed normally. Food consumption was measured on day 9 for each group.

At noon on day 10 the animals were killed by inhalation of carbon dioxide from solid carbon dioxide. A sample of blood was removed by cardiac puncture and the serum cholesterol and serum triglycerides were analysed by means of an autoanalyser.

Control groups (receiving only the normal, unmedicated diet) were included with each test.

The percentage reductions in the concentrations of serum cholesterol and serum triglycerides were calculated by comparison with the simultaneous controls, for each concentration of the test compound used.

The results obtained are shown in Table I hereafter.

TABLE I

| Compound | Form | % w/w dose in diet | % change in serum compared with control cholesterol | triglycerides |
|---|---|---|---|---|
| A | parent compound | 0.2 | −26 | −33 |
| B | parent compound | 0.2 | +5 | −4 |
| C | parent compound | 0.2 | −18 | −31 |
|   |   | 0.2 | −48 | −63 |
|   |   | 0.1 | −28 | −39 |
| C | sodium salt | 0.2 | −41 | −46 |
| D | parent compound | 0.2 | −26 | −40 |
|   |   | 0.2 | −16 | −30 |
| D | sodium salt | 0.2 | −39 | −63 |
|   |   | 0.2 | −41 | −54 |
|   |   | 0.1 | −10 | −18 |
| E | parent compound | 0.2 | −54 | −65 |
|   |   | 0.1 | −42 | −55 |
| F | parent | 0.2 | −37 | −73 |

TABLE I-continued

| Compound | Form | % w/w dose in diet | % change in serum compared with control cholesterol | triglycerides |
|---|---|---|---|---|
|   | compound | 0.1 | −18 | −43 |
| G | parent | 0.2 | −50 | −87 |
|   | compound | 0.2 | −69 | −89 |
|   |   | 0.1 | −43 | −71 |
|   |   | 0.1 | −47 | −79 |
|   |   | 0.03 | −7 | −41 |
| H | parent | 0.2 | −48 | −68 |
|   | compound | 0.1 | −15 | −26 |
| I | parent compound | 0.2 | −26 | −33 |
| J | parent compound | 0.2 | −9 | −2 |
| K | parent | 0.2 | +5 | −43 |
|   | compound | 0.2 | −17 | −26 |
| K | sodium salt | 0.2 | −17 | −60 |
|   |   | 0.2 | −22 | −42 |
| K | HCl salt | 0.2 | −25 | −52 |
| L | parent compound | 0.2 | −21 | −25 |
| L | sodium salt | 0.2 | −32 | −42 |
| U | parent compound | 0.2 | −13 | −39 |
| O | parent compound | 0.2 | −13 | −44 |
| P | parent compound | 0.2 | −32 | −37 |
| M | parent compound | 0.2 | −26 | −65 |
| R | parent compound | 0.2 | −12 | −18 |
| Q | parent compound | 0.2 | −10 | −14 |
| V | parent compound | 0.2 | +3 | −1 |
| W | parent compound | 0.2 | −3 | +22 |
| X | parent compound | 0.2 | −18 | −25 |
| Y | parent | 0.1 | −20 | −51 |
|   | compound | 0.2 | −30 | −80 |
| Z | parent compound | 0.2 | −14 | −14 |
| S | parent compound | 0.2 | −26 | −52 |
| T | parent | 0.2 | −43 | −67 |
|   | compound | 0.1 | −45 | −78 |
| AA | parent compound | 0.2 | −36 | −57 |
| NN | parent compound | 0.2 | −39 | −73 |
| G | sodium salt | 0.2 | −50 | −77 |
| OO | parent compound | 0.2 | −52 | −75 |
| PP | parent compound | 0.2 | −13 | −41 |
| QQ | parent compound | 0.2 | −16 | −36 |
| RR | parent compound | 0.2 | −7 | −88 |
| N | parent compound | 0.2 | −20 | −45 |
| S | sodium salt | 0.2 | −30 | −31 |
| SS | parent compound | 0.2 | −14 | +3 |
| TT | parent compound | 0.2 | −8 | −6 |
| UU | parent compound | 0.2 | −15 | −29 |
| VV | parent compound | 0.2 | −40 | −73 |
| BEE | parent compound | 0.2 | −19 | −18 |
| BDD | parent | 0.2 | −2 | −5 |

TABLE I-continued

| Compound | Form | % w/w dose in diet | % change in serum compared with control | |
|---|---|---|---|---|
| | | | cholesterol | triglycerides |
| BFF | parent compound | 0.2 | +7 | −17 |
| BGG | parent compound | 0.2 | −7 | −7 |
| AZZ | parent compound | 0.2 | −18 | +24 |
| Z | parent compound | 0.2 | −14 | −14 |
| W | parent compound | 0.2 | −3 | +22 |
| J | parent compound | 0.2 | −9 | −2 |
| EE | parent compound | 0.2 | −5 | −2 |
| MM | parent compound | 0.2 | +25 | −41 |
| WW | parent compound | 0.2 | −3 | +45 |
| XX | parent compound | 0.2 | −2 | +8 |
| BHH | parent compound | 0.2 | −6 | −10 |
| BCC | parent compound | 0.2 | +2 | +16 |
| AII | parent compound | 0.2 | +7 | +20 |
| AJJ | parent compound | 0.2 | −8 | +6 |
| AKK | parent compound | 0.2 | −3 | −10 |
| FF | parent compound | 0.2 | −13 | −40 |
| GG | parent compound | 0.2 | −11 | −35 |
| CC | parent compound | 0.2 | −17 | −57 |
| AMM | parent compound | 0.2 | −4 | −12 |
| ANN | parent compound | 0.2 | +1 | −25 |
| APP | parent compound | 0.2 | −2 | −20 |
| AQQ | parent compound | 0.2 | +6 | −12 |
| DD | parent compound | 0.2 | −6 | −25 |
| ARR | parent compound | 0.2 | +8 | +20 |
| ASS | parent compound | 0.2 | −2 | −20 |
| ATT | parent compound | 0.2 | −16 | −70 |
| U | parent compound | 0.2 | −13 | −39 |
| AUU | parent compound | 0.2 | −14 | −57 |
| EE | parent compound | 0.2 | −28 | −46 |
| | | 0.1 | −22 | −39 |
| KK | parent compound | 0.2 | −18 | −34 |
| AVV | parent compound | 0.2 | −21 | −80 |
| | | 0.1 | −16 | −65 |
| LL | parent compound | 0.2 | −16 | −22 |
| | | 0.1 | −13 | −32 |
| BB | parent compound | 0.2 | −19 | −39 |
| HH | parent compound | 0.2 | −24 | −50 |
| AWW | parent compound | 0.2 | −24 | — |
| ABB | parent compound | 0.2 | −18 | −34 |
| ABB | HCl salt | 0.2 | −14 | −25 |
| ACC | parent compound | 0.2 | −26 | −71 |
| YY | parent compound | 0.2 | −32 | −64 |
| YY | compound | 0.1 | −21 | −65 |
| YY | parent compound | 0.03 | −25 | −51 |
| YY | HCl salt | 0.2 | −20 | −49 |
| YY | sodium salt | 0.2 | −17 | −66 |
| AAA | parent compound | 0.2 | −12 | −55 |
| AAA | HCl salt | 0.2 | −20 | −61 |
| ADD | parent compound | 0.2 | −6 | −40 |
| AEE | parent compound | 0.2 | −22 | −37 |
| AEE | HCl salt | 0.2 | +4 | −27 |
| ZZ | parent compound | 0.2 | −32 | −77 |
| ZZ | HCl salt | 0.2 | −38 | −60 |
| AFF | parent compound | 0.2 | −38 | −58 |
| AFF | HCl salt | 0.2 | −54 | −93 |
| AFF | sodium salt | 0.2 | −39 | −84 |
| AGG | parent compound | 0.2 | −8 | −23 |
| AGG | HCl salt | 0.2 | −11 | −51 |
| K | parent compound | 0.2 | +5 | −43 |
| K | HCl salt | 0.2 | −22 | −42 |
| K | salt | 0.2 | −17 | −60 |
| K | sodium salt | 0.2 | −25 | −52 |
| BSS | parent compound | 0.2 | −9 | −11 |
| BTT | parent compound | 0.2 | 0 | +15 |
| BJJ | parent compound | 0.2 | −15 | −41 |
| BII | parent compound | 0.2 | 0 | −30 |
| CFF | parent compound | 0.2 | +6 | +10 |
| CEE | parent compound | 0.2 | −16 | −16 |
| BNN | parent compound | 0.2 | +7 | −20 |
| CCC | parent compound | 0.2 | −11 | −28 |
| BYY | parent compound | 0.2 | −23 | −50 |
| CAA | parent compound | 0.2 | −28 | −46 |
| BZZ | parent compound | 0.2 | −1 | −29 |
| CDD | parent compound | 0.2 | −19 | −41 |
| CBB | parent compound | 0.2 | +2 | −7 |
| BXX | parent compound | 0.2 | −10 | −39 |
| BQQ | parent compound | 0.2 | +11 | +31 |
| BRR | HCl salt | 0.2 | +12 | 0 |
| BOO | parent compound | 0.2 | +3 | +9 |
| BPP | parent compound | 0.2 | −3 | 0 |
| CNN | parent compound | 0.2 | −31 | −72 |
| CVV | parent | 0.1 | −16 | −56 |

TABLE I-continued

| Compound | Form compound | % w/w dose in diet | % change in serum compared with control | |
|---|---|---|---|---|
| | | | cholesterol | triglycerides |

Aortic smooth muscle cell proliferation inhibiting activity

Smooth muscle cells were grown in culture from explants of pig thoracic aorta, using Dulbecco's Modified Eagles (DME) Medium containing 20% foetal calf serum (FCS) and antibiotics. The cells were incubated at 37° C. in an atmosphere of 95% air and 5% carbon dioxide. At confluency the cells were routinely subcultured by trypsinising and replating at approximately one third of their confluent density in DME Medium containing 10% FCS and antibiotics.

The smooth muscle cells were plated out at densities of 100,000–200,000 cells per 35×10 mm Falcon dish in 2 ml DME Medium containing 10% FCS and antibiotics. After 24 hours, when the cells had attached to the dishes, the medium was replaced with 2 ml DME Medium containing 1% FCS and antibiotics. The cultures were incubated for a further three days to allow the cells to become quiescent (i.e. no longer undergoing cell division). The medium was then replaced by 2 ml control or test medium. The test medium consisted of DME Medium (containing 10% FCS and antibiotics) and the compound to be tested at a concentration of 5 µg/ml medium. The compounds were pre-dissolved in acetone such that the final concentration of acetone in the medium was 0.2% (v/v). The control medium consisted of DME Medium (containing 10% FCS and antibiotics) and acetone at 0.2% (v/v) concentration. After three days incubation in test or control medium, the medium was replaced with fresh test or control medium and the cells incubated for a further three or four days. At the end of the six or seven day incubation period cell numbers were determined by trypsinising the cells and counting the cell suspension in a Coulter counter.

All results in Table II hereafter represent the mean value for four dishes of cells. Percentage inhibition of proliferation was calculated using the following formula:

$$\text{Percentage inhibition of proliferation} = 100 - \left( \frac{T-S}{C-S} \times 100 \right)$$

where
S = Mean cell number per dish at start of experiment (upon addition of control or test medium).
T = Mean cell number per dish in test cultures at completion of experiment.
C = Mean cell number per dish in control cultures at completion of experiment.

TABLE II

| Compound | % inhibition |
|---|---|
| G | 51, 36 |
| AJJ | 45, 30 |
| YY | 78, 76, 46 |
| T | 30, 35 |
| C | 69, 45 |
| TT | 61, 64 |
| NN | 76, 78 |

TABLE II-continued

| Compound | % inhibition |
|---|---|
| ASS | 36 |

Hypoglycaemic Activity in Diabetic Mice

Diabetic mice (strain C 57, black, MRI derived Obese/Obese) of either sex each weighting between 45 and 70 g were given the test compound orally at a dose of 200 mg/kg body weight per day for 3 days. Three hours after the last dose the animals were weighed, anaesthetised with carbon dioxide and bled by cardiac puncture.

The serum glucose levels were assessed by the glucose-oxidase method of God-Perid.

Control groups (given doses of unmedicated tragacanth mucilage) were included with each test.

The percentage reduction in the concentration of serum glucose was calculated by comparison with the simultaneous controls, for each of the test compounds used.

The results obtained are shown in following Table III.

TABLE III

| Compound | % change in serum glucose compared with control |
|---|---|
| CQQ | −40 |
| BXX | −9 |

The utility of the compounds is enhanced by the fact that they are of only very low toxicity, as demonstrated in the following test:

Oral Toxicity in Mice

Groups of mice were dosed orally with graded doses of the test compound (in a 0.5% w/v aqueous suspension of tragacanth mucilage) and observed for 3 days thereafter. The percentages of animals which died during that period at each dose level were used to construct a graph, from which the LD50, that is to say the dose in mg/kg animal body weight necessary to kill 50% of the mice, was calculated.

Compounds of the present invention were tested and the LD 50 of each compound was greater than 1000 mg/kg animal body weight.

Preferred compounds of the invention are those hereinbefore identified by the letters T, C, G, F, D, VV, YY, ACC, AFF and CNN.

The compounds of general formula I may be prepared by the application or adaptation of known methods for the preparation of indole and indoline derivatives, for example by the following methods which are features of the present invention.

1. The compounds of general formula I wherein ==== represents a single bond between carbon atoms, i.e. indoline compounds of the general formula:

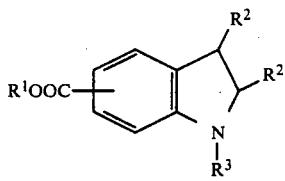

(wherein $R^1$, $R^2$ and $R^3$ are as hereinbefore defined), are prepared from compounds of general formula I wherein ---- represents a double bond between carbon atoms, i.e. indole compounds of the general formula:

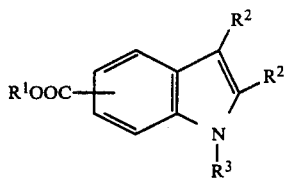

(wherein $R^1$, $R^2$ and $R^3$ are as hereinbefore defined), by reduction, for example by catalytic hydrogenation using, for example, platinum oxide or palladium on charcoal.

The reaction may be effected in the presence of a strong acid, for example fluoroboric acid or a mixture of glacial acetic acid and perchloric acid, optionally in an organic solvent, for example ethanol or tetrahydrofuran.

2. The indole compounds of general formula I represented by general formula V are prepared from indoline compounds of general formula I represented by general formula IV by catalytic dehydrogenation using, for example, palladium on charcoal in an organic solvent, for example mesitylene.

3. The indole compounds of general formula I wherein ---- represents a double bond between carbon atoms are prepared by the cyclisation of a compound of the general formula:

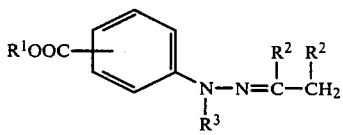

(wherein $R^1$, $R^2$ and $R^3$ are as hereinbefore defined) by reaction with an inorganic acid, for example hydrochloric acid, sulphuric acid or polyphosphoric acid, or a Lewis acid, for example boron trifluoride etherate or anhydrous zinc chloride, at an elevated temperature, for example between 70° and 150° C., optionally in the presence of an inert organic solvent for example ethanol.

4. The indole compounds of general formula I wherein ---- represents a double bond between carbon atoms, the symbol $R^2$ attached to the 2-position of the indole ring system represents a straight- or branched-chain alkyl group containing from 6 to 24 carbon atoms, the symbol $R^2$ attached to the 3-position represents a hydrogen atom, and $R^1$ and $R^3$ represent hydrogen atoms, are prepared by the cyclisation of a compound of the general formula:

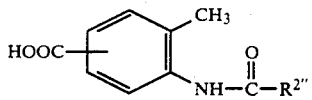

(wherein $R^{2''}$ represents a straight- or branched-chain alkyl group containing 6 to 24 carbon atoms) in the presence of a base, e.g. an alkali metal alkoxide containing from 1 to 6 carbon atoms, for example potassium tert-butoxide or sodium methoxide, or sodamide (a) at an elevated temperature, for example between 240° and 350° C. (e.g. between 290° and 305° C.) without solvent or preferably (b) at an elevated temperature, for example at from 180° to 240° C. (e.g. at the reflux temperature of the reaction mixture) in the presence of an inert organic solvent, e.g. diethylaniline.

5. The indole compounds of general formula I wherein ---- represents a double bond between carbon atoms, $R^1$ represents an optionally substituted alkyl group as hereinbefore defined, the symbol $R^2$ attached to the 2-position of the indole ring system represents a straight- or branched-chain alkyl group containing from 6 to 24 carbon atoms, the symbol $R^2$ attached to the 3-position represents a hydrogen atom, and $R^3$ is as hereinbefore defined, are prepared by the reaction of a 3-alkylthio derivative of the general formula:

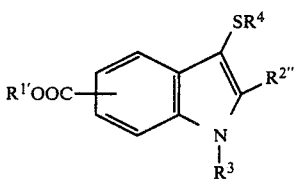

(wherein $R^{2''}$ and $R^3$ are as hereinbefore defined, $R^{1'}$ represents an optionally substituted alkyl group as hereinbefore defined for $R^1$, and $R^4$ represents a straight- or branched-chain alkyl group containing from 1 to 6 carbon atoms) with Raney nickel in the presence of an inert organic solvent, for example dioxan.

6. The indole or indoline compounds of general formula I wherein the symbol $R^2$ in the 3-position of the indole ring system represents a straight- or branched-chain alkyl group containing from 1 to 24 carbon atoms, the symbol $R^2$ attached to the 2-position represents a straight- or branched-chain alkyl group containing 6 to 24 carbon atoms, or a hydrogen atom or a straight- or branched-chain alkyl group containing 1 to 5 carbon atoms when $R^2$ in the 3-position is an alkyl group containing from 6 to 24 carbon atoms, and $R^1$ and $R^3$ are as hereinbefore defined, are prepared from compounds of the general formula:

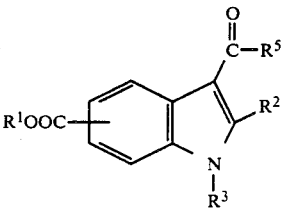

(wherein $R^1$ and $R^3$ are as hereinbefore defined, $R^5$ represents a hydrogen atom or a straight- or branched-chain alkyl group containing from 1 to 23 carbon atoms, and depicted R² represents a hydrogen atom or an alkyl group as appropriate to fit general formula (I) by reduction of the carbonyl radical to methylene using, for example, borane when it is desired to obtain a product of general formula I wherein ≈≈≈ represents a double bond between carbon atoms, or catalytic hydrogenation using, for example, palladium on charcoal, when it is desired to obtain a product of general formula I wherein ≈≈≈ represents a single bond between carbon atoms.

The reaction with borane may be effected in an anhydrous organic solvent, for example tetrahydrofuran or ethyl acetate, at an elevated temperature, e.g. at a temperature between 50° C. and the reflux temperature of the reaction mixture.

7. The indole compounds of general formula I wherein ≈≈≈ represents a double bond between carbon atoms, R¹ is as hereinbefore defined, the symbol R² attached to the 2-position of the indole ring system represents a straight- or branched-chain alkyl group containing from 6 to 24 carbon atoms, the symbol R² attached to the 3-position represents a hydrogen atom, and R³ represents a hydrogen atom, are prepared by cyclisation of a compound of the general formula:

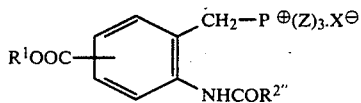

(wherein X⊖ represents an anion, preferably chloride, bromide or iodide, Z represents an optionally substituted phenyl group, and R¹ and R²″ are as hereinbefore defined) in an inert organic solvent, e.g. toluene, in the presence of a base, e.g. an alkali metal alkoxide, preferably at an elevated temperature, e.g. between 80° and 150° C.

8. The indole compounds of general formula I wherein ≈≈≈ represents a double bond between carbon atoms, R¹ is as hereinbefore defined, symbol R² attached to the 2-position of the indole ring system represents a straight- or branched-chain alkyl group containing from 6 to 24 carbon atoms, the symbol R² attached to the 3-position represents a hydrogen atom, and R³ represents a hydrogen atom, are prepared from compounds of the general formula:

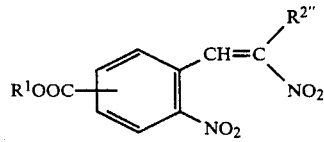

(wherein R¹ and R²″ are as hereinbefore defined) by reduction either by chemical means or by catalytic hydrogenation, followed by cyclisation of the intermediate obtained.

Chemical reduction may be effected by iron powder in an inert organic solvent in the presence of an organic acid, e.g. a mixture of ethanol and acetic acid. Catalytic hydrogenation may be effected using, for example, palladium on charcoal as catalyst, optionally in the presence of glacial acetic acid, in an organic solvent or mixtures of organic solvents.

9. The indole compounds of general formula I wherein ≈≈≈ represents a double bond between carbon atoms, R¹ is as hereinbefore defined, the symbol R² attached to the 3-position of the indole ring system represents a straight- or branched-chain alkyl group containing from 6 to 24 carbon atoms, the symbol R² attached to the 2-position represents a hydrogen atom and R³ is as hereinbefore defined, are prepared from 2-alkoxycarbonyl derivatives of the general formula:

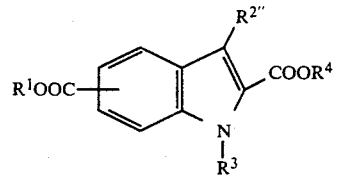

(wherein R¹, R²″, R³ and R⁴ are as hereinbefore defined) by decarboxylation with heating.

10. The carboxylic acids of general formula I (wherein R¹ represents a hydrogen atom, and R² and R³ are as hereinbefore defined) are prepared by hydrolysis of the corresponding esters of formula I wherein R² and R³ are as hereinbefore defined and R¹ represents an optionally substituted straight- or branched-chain alkyl group containing from 1 to 6 carbon atoms. Preferably the hydrolysis is carried out in alkaline conditions, for example in the presence of an alkali metal hydroxide in an aqueous organic solvent system, and at an elevated temperature, e.g. in the presence of sodium hydroxide, in aqueous methanol or ethanol and at the reflux temperature.

11. The esters of general formula I (wherein R¹ represents an optionally substituted straight- or branched-chain alkyl group containing from 1 to 6 carbon atoms, and R² and R³ are as hereinbefore defined) are prepared by esterification of the corresponding carboxylic acids of general formula I wherein R¹ represents a hydrogen atom, and R² and R³ are as hereinbefore defined. The esterification may be carried out by the application or adaptation of known methods, for example by reaction with an excess of the appropriate alcohol of the general formula:

R¹′OH          XIII (wherein R¹′ represents an optionally substituted -as hereinbefore specified- straight- or branched-chain alkyl group containing from 1 to 6 carbon atoms) optionally as the solvent medium, and in the presence of an inorganic acid, e.g. hydrochloric acid, preferably at an elevated temperature, e.g. between 60° and 100° C. or by reaction of a corresponding alkyl halide and salt of the acid.

12. The tertiary amine compounds of general formula I wherein the depicted nitrogen atom is alkylated are prepared by N-alkylation of the corresponding secondary amine compounds of general formula I (wherein R³ represents a hydrogen atom) by the application or adaptation of known methods.

By the term "known methods" as used in this specification is meant methods heretofore used or described in the literature.

13. The compounds of general formula I may be converted, when applicable, to pharmaceutically acceptable salts, and vice versa, by the application or adaptation of known methods.

As well as being useful in itself, this procedure is useful for the purification of compounds of general formula I and their salts by taking advantage of differences in solubility in water and various organic solvents of the compounds and their salts and of any impurities present by means of known methods, such as crystallisation.

(i) Compounds of general formula I wherein  represents a single bond between carbon atoms may be converted to their pharmaceutically acceptable acid addition salts, for example, by reaction with the appropriate acid in solution or suspension in a suitable solvent, e.g. acetone, methanol or ethanol, followed if necessary by evaporation of part or all of the solvent, and collection of the solid salt.

(ii) On the other hand, the acid addition salts may be converted to the parent compounds of general formula I, for example by reaction with aqueous ammonia in the presence of a suitable solvent, e.g. ethanol, followed by treatment with a weak acid, for example glacial acetic acid.

(iii) Compounds of general formula I wherein $R^1$ represents a hydrogen atom ($R^2$ and $R^3$ being as hereinbefore defined) may be converted to their salts of pharmaceutically acceptable bases, for example by reaction with the appropriate base, for example the appropriate amine or a compound of the general formula:

$$M^1 OR^6 \qquad (XIV)$$

(wherein $M^1$ represents an alkali metal, e.g. sodium or potassium, and $R^6$ represents an alkyl group containing from 1 to 6 carbon atoms, e.g. methyl or ethyl, or a hydrogen atom) in a suitable solvent, e.g. methanol or ethanol, or water followed if necessary by evaporation of part or all of the solvent, and collection of the solid salt.

(iv) Salts obtained as described in (iii) above may be converted to the parent acids of general formula I (wherein $R^1$ represents a hydrogen atom), for example by reaction with a suitable acid, e.g. glacial acetic acid, in solution in a suitable solvent, e.g. water or ethanol, followed if necessary by evaporation of part or all of the solvent, and collection of the solid acid.

Compounds of general formula VI may be prepared by the reaction of a compound of the general formula:

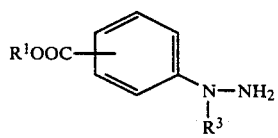

XV (wherein $R^1$ and $R^3$ are as hereinbefore defined) with a compound of the general formula:
$$O=CR^2-CH_2R^2 \qquad XVI$$

(wherein the symbols $R^2$ are as hereinbefore defined) at an elevated temperature, e.g. at the reflux temperature of the reaction mixture, in an inert organic solvent, e.g. ethanol, in the presence of glacial acetic acid as catalyst, preferably under an inert atmosphere, e.g. nitrogen.

Compounds of general formula VII may be prepared by the reaction of a compound of the general formula:

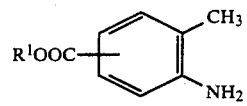

XVII (wherein $R^1$ is as hereinbefore defined) with an acylating agent of the general formula:

$$R^{2''}COX^1 \qquad XVIII$$

(wherein $R^{2''}$ is as hereinbefore defined and $X^1$ represents a halogen, preferably chlorine, atom or a hydroxy group) optionally in an inert organic solvent, for example dimethylformamide or chloroform, at a temperature between 0° C. and the reflux temperature of the reaction mixture, preferably under anhydrous conditions and optionally in the presence of an acid-binding agent, for example a trialkylamine, e.g. triethylamine or tributylamine, followed by hydrolysis of the ester to the corresponding acid.

Compounds of general formula VIII may be prepared by the reaction of a compound of the general formula:

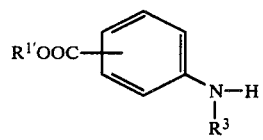

XIX (wherein $R^{1'}$ and $R^3$ are as hereinbefore defined) with a compound of the general formula:

$$O=CR^{2''}-CH_2SR^4 \qquad XX$$

(wherein $R^{2''}$ and $R^4$ are as hereinbefore defined) at a temperature between −65° C. and ambient temperature in an inert organic solvent e.g. methylene chloride, in the presence of tert.-butyl hypochlorite and of organic base e.g. triethylamine.

Compounds of general formula IX may be prepared by the reaction of a compound of the general formula:

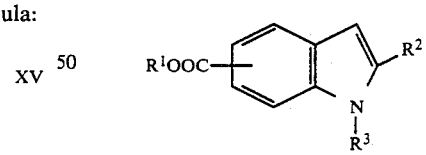

XXI (wherein $R^1$ and $R^3$ are as hereinbefore defined and the depicted symbol $R^2$ is as hereinbefore defined for general formula IX) with a compound of the general formula:

$$O=C(R^5)N(R^4)_2 \qquad XXII$$

(wherein $R^4$ and $R^5$ are as hereinbefore defined) in the presence of phosphorus oxychloride at an elevated temperature, e.g. at a temperature between 50° C. and 90° C.

Compounds of general formula X may be prepared by reacting a compound of the general formula:

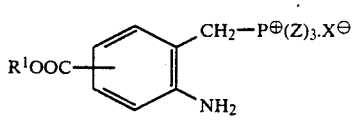 XXIII (wherein R¹, X⊖ and Z are as hereinbefore defined) with a compound of general formula XVIII.

Compounds of general formula XI may be prepared by nitrating a compound of the general formula:

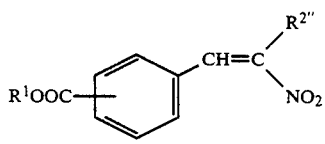 XXIV wherein R¹ and R²″ are as hereinbefore defined.

Compounds of general formula XXIV may be prepared by reacting a compound of general formula:

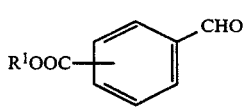 XXV (wherein R¹ is as hereinbefore defined) with a compound of general formula:

R²″CH₂NO₂   XXVI (wherein R²″ is as hereinbefore defined) in the presence of an organic base at the reflux temperature of the reaction mixture with continuous removal of the water produced.

Compounds of general formula XII may be prepared from compounds of the general formula:

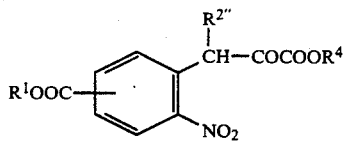 XXVII (wherein R¹, R²″ and R⁴ are as hereinbefore defined) by reduction either by chemical means or by catalytic hydrogenation, followed if necessary by N-alkylation of the resulting indole compound by known methods.

Chemical reduction may be effected by zinc dust in acetic acid at an elevated temperature.

Catalytic hydrogenation may be effected using, for example, palladium on charcoal as catalyst in an organic solvent or mixtures thereof.

Compounds of general formula XXVII may be prepared by R²″-alkylation of the corresponding compounds of the general formula:

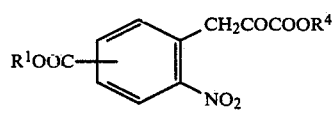 XXVIII (wherein R¹ and R⁴ are as hereinbefore defined) by the application or adaptation of known methods.

Compounds of general formula XXVIII may be prepared by reacting a compound of the general formula:

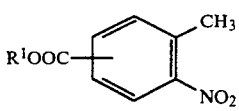 XXIX (wherein R¹ is as hereinbefore defined) with oxalic acid dialkyl ester in the presence of alkali metal alkoxide.

It will be understood by those skilled in the art that in the performance of the processes described above of the present invention it may be desirable to introduce chemical protecting groups into the reactants in order to avoid secondary reactions taking place, for example, in the methods of preparation of indole derivatives hereinbefore described hydroxy substituent(s) on an alkyl group R¹ as defined in relation to general formula I may have been converted into benzyloxy groups before reaction as described with subsequent removal of the protecting benzyl groups.

The following Examples illustrate the preparation of the compounds of the present invention.

EXAMPLE 1

Compound D

A mixture of 3-(n-hexadecanamido)-4-methylbenzoic acid (6.0 g) and potassium tert-butoxide (22.0 g) was placed in a preheated Woods Metal bath (temperature range 240°–260° C.). The temperature of the bath was rapidly raised to between 290° and 305° C. and was maintained within this region for 15 minutes. The mixture was then left to cool to room temperature. Water (100 ml) was added to the mixture and the resultant suspension was treated with dilute hydrochloric acid (100 ml of strength 2N) and the mixture was extracted with diethyl ether (3×100 ml). The organic extract was washed with water (2×100 ml), dried over magnesium sulphate and was evaporated in vacuo to give a solid. The solid was recrystallised from glacial acetic acid and then toluene to give 2-(n-pentadecyl)indole-6-carboxylic acid (3.05 g), in the form of an off-white solid, m.p. 140°–142° C.

(i) The 3-(n-hexadecanamido)-4-methylbenzoic acid, used as starting material, was prepared as follows:

A stirred solution of 3-amino-4-methylbenzoic acid (15.1 g) in dry dimethylformamide (150 ml), containing triethylamine (20.2 g) was treated with n-hexadecanoyl chloride (27.5 g) during 30 minutes. The temperature of the reaction mixture was maintained at 25°–45° C. during the addition by water cooling. The mixture was then stirred for a further hour and was poured into water (1000 ml). The mixture was adjusted to pH 1 by the addition of concentrated hydrochloric acid (strength 0.6% w.v). The solid was collected, was washed with water and was recrystallised from ethanol (1500 ml) to give 3-(n-hexadecanamido)-4-methylbenzoic acid (22.0 g), in the form of a white solid, m.p. 238°–240° C.

EXAMPLE 2

Compound G

A mixture of 4-(n-hexadecanamido)-3-methylbenzoic acid (6.3 g) and potassium tert-butoxide (25 g) was treated in a similar manner to that described hereinbefore in Example 1 to give 2-(n-pentadecyl)indole-5-carboxylic acid (3.6 g), in the form of a white solid, m.p. 110°–112° C.

(i) The 4-(n-hexadecanamido)-3-methylbenzoic acid, used as starting material, was prepared as follows:

A stirred solution of 4-amino-3-methylbenzoic acid (30.2 g), in dry dimethylformamide (300 ml), containing tributylamine (55 ml) was treated with n-hexadecanoyl chloride (61.0 g) in a similar manner to that described in Example 1(i) to give 4-(n-hexadecanamido)-3-methylbenzoic acid (21 g), in the form of white needles, m.p. 194°–196° C.

EXAMPLE 3

Compound J

A mixture of 3-(n-hexadecanamido)-2-methylbenzoic acid (6.0 g) and potassium tert-butoxide (23 g) was treated in a similar manner to that described hereinbefore in Example 1 to give 2-(n-pentadecyl)indole-4-carboxylic acid (3.1 g), in the form of a cream solid, m.p. 114°–117° C.

(i) The 3-(n-hexadecanamido)-2-methylbenzoic acid, used as starting material, was prepared as follows:

A stirred solution of ethyl 3-amino-2-methylbenzoate (17.9 g) in chloroform (150 ml), containing triethylamine (15 ml), was treated with a solution of n-hexadecanoyl chloride (28 g) in chloroform (50 ml), during 30 minutes. The temperature of the reaction mixture was maintained at 0°–10° C. during the addition by ice cooling. The mixture was then refluxed for 90 minutes, washed with water (2×150 ml) and was dried over magnesium sulphate. The solvent was removed in vacuo to give a white solid, which was recrystallised from ethanol. The solid was dissolved in warm ethanol (500 ml) and the solution was treated with sodium hydroxide (10 g) in water (50 ml). The mixture was then refluxed for one hour and was poured onto a mixture of crushed ice and dilute hydrochloric acid (150 ml of strength 2N). The solid was collected and was recrystallised from ethanol (1000 ml) to give 3-(n-hexadecanamido)-2-methylbenzoic acid (28 g), in the form of a white solid, m.p. 163°–165° C.

EXAMPLE 4

Compound I

A mixture of 2-(n-hexadecanamido)-3-methylbenzoic acid (5.0 g) and potassium tert-butoxide (20 g) was treated in a similar manner to that described in Example 1 to give a solid, which was recrystallised from methanol to give 2-(n-pentadecyl)indole-7-carboxylic acid (4.25 g), in the form of a white solid, m.p. 93°–99° C.

The 2-(n-hexadecanamido)-3-methylbenzoic acid, used as starting material, was prepared as follows:

A stirred solution of 2-amino-3-methylbenzoic acid (31.4 g) in dry dimethylformamide (300 ml), containing tributylamine (60 ml) was treated in a similar manner to that described in Example 1(i) to give 2-(n-hexadecanamido)-3-methylbenzoic acid (8.7 g), in the form of a white solid, m.p. 106°–113° C.

EXAMPLE 5

Compound L

A mixture of 3-(n-decanamido)-4-methylbenzoic acid (6.0 g) and potassium tert-butoxide (23.5 g) was treated in a similar manner to that described hereinbefore in Example 1 to give a solid which was recrystallised from ethanol to give 2-(n-nonyl)indole-6-carboxylic acid (4.1 g), in the form of colourless crystals, m.p. 166°–169° C.

(i) The 3-(n-decanamido)-4-methylbenzoic acid, used as starting material, was prepared as follows:

A solution of 3-amino-4-methylbenzoic acid (15.1 g) and n-decanoyl chloride (19.4 g) in dry dimethylformamide (150 ml) was heated on a steam bath for 90 minutes. The solution was poured into water and the solid was collected, and recrystallised from ethanol (600 ml) to give 3-(n-decanamido)-4-methylbenzoic acid (22.5 g), in the form of a white powder, m.p. 246°–250° C.

EXAMPLE 6

Compound A

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-tetradecanamido)-4-methylbenzoic acid, there was prepared 2-(n-tridecyl)indole-6-carboxylic acid, in the form of colourless plates, m.p. 151°–153° C.

By proceeding in a similar manner to that hereinbefore described in Example 1(i) for the preparation of 3-(n-hexadecanamido)-4-methylbenzoic acid but replacing n-hexadecanoyl chloride by n-tetradecanoyl chloride and triethylamine by tributylamine, there was prepared 3-(n-tetradecanamido)-4-methylbenzoic acid, in the form of a colourless solid, m.p. 233°–235° C., used in the preparation above.

EXAMPLE 7

Compound B

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-octadecanamido)-4-methylbenzoic acid, there was prepared 2-(n-heptadecyl)indole-6-carboxylic acid, in the form of colourless crystals, m.p. 134°–136° C.

By proceeding in a similar manner to that hereinbefore described in Example 1(i) for the preparation of 3-(n-hexadecanamido)-4-methylbenzoic acid but replacing n-hexadecanoyl chloride by n-octadecanoyl chloride and triethylamine by tributylamine, there was prepared 3-(n-octadecanamido)-4-methylbenzoic acid, in the form of a white powder, m.p. 228°–231° C., used in the preparation above.

EXAMPLE 8

Compound C

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-dodecanamido)-4-methylbenzoic acid, there was prepared 2-(n-undecyl)indole-6-carboxylic acid, in the form of colourless plates, m.p. 156°–159° C.

By proceeding in a similar manner to that hereinbefore described in Example 3(i) for the preparation of 3-(n-hexadecanamido)-2-methylbenzoic acid but replacing ethyl 3-amino-2-methylbenzoic acid by ethyl 3-amino-4-methylbenzoic acid, n-hexadecanoyl chloride by n-dodecanoyl chloride and triethylamine by tributylamine, there was prepared 3-(n-dodecanamido)-4-methylbenzoic acid, in the form of colourless crystals, m.p. 240°–243° C., used in the preparation above.

EXAMPLE 9

Compound E

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-octadecanamido)-3-methylbenzoic acid, there was prepared 2-(n-heptadecyl)indole-5-carboxylic acid, in the form of a white solid, m.p. 108°–111° C.

By proceeding in a similar manner to that hereinbefore described in Example 2(i) for the preparation of 4-(n-hexadecanamido)-3-methylbenzoic acid but replacing n-hexadecanoyl chloride by n-octadecanoyl chloride, there was prepared 4-(n-octadecanamido)-3-methylbenzoic acid, in the form of a white powder, m.p. 192°–196° C., used in the preparation above.

EXAMPLE 10

Compound F

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-dodecanamido)-3-methylbenzoic acid, there was prepared 2-(n-undecyl)indole-5-carboxylic acid, in the form of light brown crystals, m.p. 124°–126° C.

By proceeding in a similar manner to that hereinbefore described in Example 2(i) for the preparation of 4-(n-hexadecanamido)-3-methylbenzoic acid but replacing n-hexadecanoyl chloride by n-dodecanoyl chloride and tributylamine by triethylamine, there was prepared 4-(n-dodecanamido)-3-methylbenzoic acid, in the form of a colourless solid, m.p. 192°–196° C., used in the preparation above.

EXAMPLE 11

Compound H

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-tetradecanamido)-3-methylbenzoic acid, there was prepared 2-(n-tridecyl)indole-5-carboxylic acid, in the form of light brown crystals, m.p. 124°–126° C.

By proceeding in a similar manner to that hereinbefore described in Example 2(i) for the preparation of 4-(n-hexadecanamido)-3-methylbenzoic acid but replacing n-hexadecanoyl chloride by n-tetradecanoyl chloride there was prepared 4-(n-tetradecanamido)-3-methylbenzoic acid, in the form of a white powder, m.p. 197°–200° C., used in the preparation above.

EXAMPLE 12

Compound M

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-undecanamido)-3-methylbenzoic acid, there was prepared 2-(n-decyl)indole-5-carboxylic acid, in the form of a light orange solid, m.p. 127°–130° C.

By proceeding in a similar manner to that hereinbefore described in Example 2(i) for the preparation of 4-(n-hexadecanamido)-3-methylbenzoic acid but replacing n-hexadecanoyl chloride by n-undecanoyl chloride, there was prepared 4-(n-undecanamido)-3-methylbenzoic acid, in the form of a white solid, m.p. 197°–200° C., used in the preparation above.

EXAMPLE 13

Compound N

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-undecanamido)-4-methylbenzoic acid, there was prepared 2-(n-decyl)indole-6-carboxylic acid, in the form of a cream solid, m.p. 160°–164° C.

By proceeding in a similar manner to that hereinbefore described in Example 1(i) for the preparation of 3-(n-hexadecanamido)-4-methylbenzoic acid but replacing n-hexadecanoyl chloride by n-undecanoyl chloride and triethylamine by tributylamine, there was prepared 3-(n-undecanamido)-4-methylbenzoic acid, in the form of a white solid, m.p. 242°–246° C., used in the preparation above.

EXAMPLE 14

Compound O

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-decanamido)-3-methylbenzoic acid, there was prepared 2-(n-nonyl)indole-5-carboxylic acid, in the form of a light brown solid, m.p. 137°–141° C.

By proceeding in a similar manner to that hereinbefore described in Example 2(i) for the preparation of 4-(n-hexadecanamido)-3-methylbenzoic acid but replacing n-hexadecanoyl chloride by n-decanoyl chloride, there was prepared 4-(n-decanamido)-3-methylbenzoic acid, in the form of a colourless powder, m.p. 196°–199° C., used in the preparation above.

EXAMPLE 15

Compound P

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-nonanamido)-4-methylbenzoic acid, there was prepared 2-(n-octyl)indole-6-carboxylic acid, in the form of colourless crystals, m.p. 166°–169° C.

By proceeding in a similar manner to that hereinbefore described in Example 1(i) for the preparation of 3-(n-hexadecanamido)-4-methylbenzoic acid but replacing n-hexadecanoyl chloride by n-nonanoyl chloride, there was prepared 3-(n-nonanamido)-4-methylbenzoic acid, in the form of a white solid, m.p. 247°–250° C., used in the preparation above.

EXAMPLE 16

Compound Q

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-octanamido)-3-methylbenzoic acid, there was prepared 2-(n-heptyl)indole-5-carboxylic acid, in the form of a light brown solid, m.p. 152°–155° C.

By proceeding in a similar manner to that hereinbefore described in Example 5(i) for the preparation of 3-(n-decanamido)-4-methylbenzoic acid but replacing 3-amino-4-methylbenzoic acid by 4-amino-3-methylbenzoic acid and n-decanoyl chloride by n-octanoyl chloride, there was prepared 4-(n-octanamido)-3-methylbenzoic acid, in the form of colourless needles, m.p. 221°–224° C., used in the preparation above.

EXAMPLE 17

Compound R

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-octanamido)-4-methylbenzoic acid, there was prepared 2-(n-heptyl)indole-6-carboxylic acid, in the form of a cream solid, m.p. 169°–172° C.

By proceeding in a similar manner to that hereinbefore described in Example 5(i) for the preparation of 3-(n-decanamido)-4-methylbenzoic acid but replacing n-decanoyl chloride by n-octanoyl chloride, there was prepared 3-(n-octanamido)-4-methylbenzoic acid, in the form of a white solid, m.p. 246°–250° C., used in the preparation above.

EXAMPLE 18

Compound K 2-(n-Pentadecyl)indole-6-carboxylic acid (16.0 g) was dissolved in a mixture of tetrahydrofuran (400 ml) and ethanol (100 ml), containing aqueous fluoroboric acid (100 ml, of strength 40% w/v). The stirred mixture was hydrogenated over platinum oxide (2.0 g) at room temperature and atmospheric pressure. After 6 hours the mixture was filtered, the residue was washed with diethyl ether (100 ml) and the combined filtrates were concentrated in vacuo until a solid separated. The mixture was adjusted to pH 7 by treatment with an aqueous solution of sodium hydroxide (strength 50% w/v) and was then adjusted to pH 4–5 with glacial acetic acid. The mixture was extracted with diethyl ether (3×100 ml), and the ether solution was dried over magnesium sulphate and, on evaporation in vacuo, gave a solid. The solid was recrystallised from a mixture of toluene and hexane (equal parts by volume) to give (RS)-2-(n-pentadecyl)-indoline-6-carboxylic acid (7.3 g), in the form of a colourless solid, m.p. 119°–122° C.

The corresponding hydrochloride salt was prepared as follows:

A solution of (RS)-2-(n-pentadecyl)indoline-6-carboxylic acid (3.0 g) in ethanol (30 ml), was treated with a saturated solution of hydrogen chloride gas in ethanol (50 ml of strength 34% w/v). Anhydrous diethyl ether was then added to the mixture until a solid separated. The solid was collected and was washed with diethyl ether (2×100 ml) to give (RS)-2-(n-pentadecyl)indoline-6-carboxylic acid hydrochloride (2.7 g), in the form of a colourless solid, m.p. 230°–240° C. (with decomposition).

The sodium salt of (RS)-2-(n-pentadecyl)-indoline-6-carboxylic acid was prepared as follows:

(RS)-2-(n-pentadecyl)indoline-6-carboxylic acid (10.0 g) in hot ethanol (250 ml) was treated with an aqueous sodium hydroxide solution (20 ml, of strength 10% w/v). The mixture was left to cool and a solid precipitated and was collected. The solid was washed with a little water and then acetone and was recrystallised from a mixture of ethanol and water (95:5) to give sodium (RS)-2-(n-pentadecyl)indoline-6-carboxylate (4.9 g), in the form of colourless crystals, m.p. greater than 320° C. (with decomposition).

EXAMPLE 19

Compound S

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-tridecanamido)-4-methylbenzoic acid, there was prepared 2-(n-dodecyl)indole-6-carboxylic acid, in the form of a white solid, m.p. 153°–156° C.

By proceeding in a similar manner to that hereinbefore described in Example 5(i) for the preparation of 3-(n-decanamido)-4-methylbenzoic acid but replacing n-decanoyl chloride by n-tridecanoyl chloride there was prepared 3-(n-tridecanamido)-4-methylbenzoic acid, in the form of a white solid, m.p. 243°–247° C., used in the preparation above.

EXAMPLE 20

Compound T

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-nonadecanamido)-3-methylbenzoic acid, there was prepared 2-(n-octadecyl)indole-5-carboxylic acid, in the form of a white solid m.p. 116°–118° C.

By proceeding in a similar manner to that hereinbefore described in Example 5(i) for the preparation of 3-(n-decanamido)-4-methylbenzoic acid but replacing 3-amino-4-methylbenzoic acid by 4-amino-3-methylbenzoic acid and n-decanoyl chloride by n-nonadecanoyl chloride there was prepared 4-(n-nonadecanamido)-3-methylbenzoic acid, in the form of colourless plates, m.p. 197°–199° C., used in the preparation above.

EXAMPLE 21

Compound U

A solution of 2-(n-undecyl)indole-5-carboxylic acid (15.0 g) in ethanol (50 ml) containing a solution of hydrogen chloride gas in ethanol (100 ml of strength 34% w/v) was refluxed for 3 hours. The solution was poured onto a mixture of crushed ice and water and the precipitated solid was collected. Recrystallisation from ethanol (100 ml) with charcoal treatment gave ethyl 2-(undecyl)indole-5-carboxylate (7.5 g), in the form of white crystals, m.p. 76°–77° C.

EXAMPLE 22

Compound AA

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-heneicosanamido)-3-methylbenzoic acid, there was prepared 2-(n-eicosyl)indole-5-carboxylic acid, in the form of a buff solid, m.p. 110°–112° C.

By proceeding in a similar manner to that hereinbefore described in Example 5(i) for the preparation of 3-(n-decanamido)-4-methylbenzoic acid but replacing 3-amino-4-methylbenzoic acid by 4-amino-3-methylbenzoic acid and n-decanoyl chloride by n-heneicosanoyl chloride, there was prepared 4-(n-heneicosanamido)-3-methylbenzoic acid, in the form of a buff solid, m.p. 189°–193° C., used in the preparation above.

EXAMPLE 23

Compound V

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-nonadecanamido)-4-methylbenzoic acid there was prepared 2-(n-octadecyl)indole-6-carboxylic acid, in the form of a pale yellow solid, m.p. 129°–131° C.

By proceeding in a similar manner to that hereinbefore described in Example 5(i) for the preparation of 3-(n-decanamido)-4-methylbenzoic acid but replacing n-decanoyl chloride by a n-nonadecanoyl chloride there was prepared 3-(n-nonadecanamido)-4-methylbenzoic acid, in the form of a buff solid m.p. 233°–236° C., used in the preparation above.

EXAMPLE 24

Compound W

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-dodecanamido)-2-methylbenzoic acid, there was prepared 2-(n-undecyl)indole-4-carboxylic acid, in the form of a cream solid, m.p. 108°–111° C.

By proceeding in a similar manner to that hereinbefore described in Example 3(i) for the preparation of 3-(n-hexadecanamido)-2-methylbenzoic acid but replacing n-hexadecanoyl chloride by n-dodecanoyl chloride, there was prepared 3-(n-dodecanamido)-2-methylbenzoic acid, in the form of a white powder, m.p. 162°–166° C., used in the preparation above.

EXAMPLE 25

Compound X

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-nonanamido)-3-methylbenzoic acid, there was prepared 2-(n-octyl)indole-5-carboxylic acid, in the form of a cream solid, m.p. 136°–138° C.

By proceeding in a similar manner to that hereinbefore described in Example 5(i) for the preparation of 3-(n-decanamido)-4-methylbenzoic acid but replacing 3-amino-4-methylbenzoic acid by 4-amino-3-methylbenzoic acid and n-decanoyl chloride by n-nonanoyl chloride there was prepared 4-(n-nonanamido)-3-methylbenzoic acid, in the form of a white crystalline solid, m.p. 196°–199° C., used in the preparation above.

EXAMPLE 26

Compound Y

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-tridecanamido)-3-methylbenzoic acid, there was prepared 2-(n-dodecyl)indole-5-carboxylic acid, in the form of a cream solid, m.p. 114°–117° C.

By proceeding in a similar manner to that hereinbefore described in Example 5(i) for the preparation of 3-(n-decanamido)-4-methylbenzoic acid but replacing 3-amino-4-methylbenzoic acid by 4-amino-3-methylbenzoic acid and n-decanoyl chloride by n-tridecanoyl chloride, there was prepared 4-(n-tridecanamido)-3-methylbenzoic acid, in the form of a white crystalline solid, m.p. 201°–203° C., used in the preparation above.

EXAMPLE 27

Compound Z

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-decanamido)-2-methylbenzoic acid, there was prepared 2-(n-nonyl)indole-4-carboxylic acid, in the form of a pale yellow solid, m.p. 92°–94° C.

By proceeding in a similar manner to that hereinbefore described in Example 3(i) for the preparation of 3-(n-hexadecanamido)-2-methylbenzoic acid but replacing n-hexadecanoyl chloride by n-decanoyl chloride there was prepared 3-(n-decanamido)-2-methylbenzoic acid, in the form of a cream solid, m.p. 160°–164° C., used in the preparation above.

EXAMPLE 28

Compound CC

A solution of 2-(n-dodecyl)indole-6-carboxylic acid (14.0 g) in ethanol (70 ml) containing a solution of hydrogen chloride gas in ethanol (100 ml, of strength 35% w/v) was refluxed for 5 hours. The solid, which crystallised on cooling, was collected, washed with light petroleum ether (b.p. 40°–60° C.) and was recrystallised from ethanol to give ethyl 2-(n-dodecyl)-indole-6-carboxylate (9.1 g), in the form of a pale pink solid, m.p. 83°–86° C.

EXAMPLE 29

Compound DD

A solution of 2-(n-heptyl)indole-5-carboxylic acid (18.4 g) in ethanol (80 ml) containing a solution of hydrogen chloride gas in ethanol (110 ml, of strength 34% w/v) was refluxed for 6 hours. The solution was poured into water and the solid was collected and was recrystallised from methanol to give ethyl 2-(n-heptyl)indole-5-carboxylate (10.7 g), in the form of buff crystals, m.p. 66°–69° C.

EXAMPLE 30

Compound EE

A solution of 2-(n-pentadecyl)indole-4-carboxylic acid (15 g) in ethanol (100 ml) containing a solution of hydrogen chloride gas in ethanol (100 ml, of strength 35% w/v) was refluxed for 6 hours. After cooling, the solution was poured into water and the solid was collected and was recrystallised from methanol to give ethyl 2-(n-pentadecyl)indole-4-carboxylate (12.4 g), in the form of a pale yellow solid, m.p. 42°–45° C.

EXAMPLE 31

Compound JJ

A solution of 2-(n-undecyl)indole-6-carboxylic acid (15.0 g) in methanol (200 ml) containing aqueous hydrochloric acid (10 ml of strength 36.5% w/v) was refluxed for 8 hours. The solution was concentrated in vacuo to about one half of its volume, diluted with diethyl ether (300 ml) and washed with water. The solution was dried over magnesium sulphate, then evaporated in vacuo and the residue was recrystallised from methanol to give methyl 2-(n-undecyl)indole-6-carboxylate (10.5 g), in the form of an off-white powder, m.p. 84°–86° C.

EXAMPLE 32

Compound KK

A solution of 2-(n-dodecyl)indole-5-carboxylic acid (15.0 g) in n-butanol (100 ml) containing aqueous hydrochloric acid (10ml of strength 36.5% w/v) was heated on a steam bath for 8 hours. The solution was concentrated in vacuo to about one half of its volume, diethyl ether (300 ml) was added, and the solution was washed with water and was dried over magnesium sulphate. Evaporation of the solvent in vacuo gave a residue which was recrystallised from methanol to give n-butyl 2-(n-dodecyl)indole-5-carboxylate (9.6 g), in the form of an off-white powder, m.p. 74°–76° C.

EXAMPLE 33

Compound II

A solution of 2-(n-dodecyl)indole-5-carboxylic acid (13.8 g) in ethanol (80 ml) containing a solution of hydrogen chloride gas in ethanol (100 ml of strength 39% w/v) was refluxed for 6 hours. The solid which separated on cooling was collected and was recrystallised from ethanol to give ethyl 2-(n-dodecyl)indole-5-carboxylate (11.2 g), in the form of a buff powder, m.p. 77°–79° C.

EXAMPLE 34

Compound HH

A solution of 2-(n-pentadecyl)indole-5-carboxylic acid (17.4 g) in n-butanol (100 ml) containing aqueous hydrochloric acid (10 ml of strength 36.5% w/v) was heated in a steam bath for 18 hours. The solution was concentrated in vacuo to about one half of its volume and the residue was dissolved in diethyl ether. The ethereal solution was washed with water (2×50 ml) and was dried over magnesium sulphate. Evaporation of the solvent in vacuo gave a solid, which was recrystallised from light petroleum ether (b.p. 40°–60° C.) and then from methanol to give n-butyl 2-(n-pentadecyl)indole-5-carboxylate (12.2 g), in the form of a white powder, m.p. 79°–80° C.

EXAMPLE 35

Compound GG

A solution of 2-(n-undecyl)indole-6-carboxylic acid (15.0 g) in n-butanol (100 ml) containing aqueous hydrochloric acid (10 ml, of strength 36.5% w/v) was heated on a steam bath for 16 hours. The solution was concentrated in vacuo to approximately half of its volume and the solid which crystallised on cooling was collected and washed with light petroleum ether (b.p. 40°–60° C.) to give n-butyl 2-(n-undecyl)-indole-6-carboxylate (11.3 g), in the form of white crystals, m.p. 73°–76° C.

EXAMPLE 36

Compound FF

A solution of 2-(n-undecyl)indole-6-carboxylic acid (11.9 g) in ethanol (50 ml) containing a solution of hydrogen chloride gas in ethanol (75 ml, of strength 39% w/v) was refluxed for 4.5 hours. The solution was cooled and a solid was collected which was dissolved in diethyl ether, and the ethereal solution was washed with water (2×100 ml) and dried over magnesium sulphate. The solvent was removed in vacuo to give a residue which was recrystallised from methanol to give ethyl 2-(n-undecyl)indole-6-carboxylate (6.2 g), in the form of very pale yellow needles, m.p. 84°–86° C.

EXAMPLE 37

Compound LL

A solution of 2-(n-pentadecyl)indole-5-carboxylic acid (15.0 g) in methanol (100 ml) containing aqueous hydrochloric acid (10 ml, of strength 36.5% w/v) was refluxed for 5 hours. After cooling, the mixture was dissolved in a mixture of diethyl ether and tetrahydrofuran (1:1). The solution was washed with water (2×50 ml), dried over sodium sulphate, evaporated in vacuo, and the residue was recrystallised from methanol to give methyl 2-(n-pentadecyl)indole-5-carboxylate (12.2 g), in the form of an off-white powder, m.p. 89°–92° C.

EXAMPLE 38

Compound BB

By proceeding in a similar manner to that hereinbefore described in Example 33 for the preparation of ethyl 2-(n-dodecyl)indole-5-carboxylate but replacing 2-(n-dodecyl)indole-5-carboxylate acid by 2-(n-pentadecyl)indole-5-carboxylic acid, there was prepared ethyl 2-(n-pentadecyl)indole-5-carboxylate, in the form of off-white crystals m.p. 88°–91° C.

EXAMPLE 39

Compound D

A solution of 2-(n-pentadecyl)indole-6-carboxylic acid (15.0 g) in hot ethanol (100 ml) was treated with a solution of sodium hydroxide (2.0 g) in water (50 ml), and a white precipitate was obtained. The precipitate was recrystallised from aqueous ethanol (1:1) (300 ml) to give sodium 2-(n-pentadecyl)-indole-6-carboxylate (14.8 g), in the form of white crystals, m.p. greater than 340° C.

EXAMPLE 40

Compound C

By proceeding in a similar manner to that hereinbefore described in Example 39 for the preparation of sodium 2-(n-pentadecyl)indole-6-carboxylate but replacing 2-(n-pentadecyl)indole-6-carboxylic acid by 2-(n-undecyl)indole-6-carboxylic acid there was prepared sodium 2-(n-undecyl)indole-6-carboxylate, in the form of colourless needles, m.p. greater than 340° C.

EXAMPLE 41

Compound MM

By proceeding in a similar manner to that hereinbefore described in Example 35 for the preparation of n-butyl 2-(n-undecyl)indole-6-carboxylate but replacing 2-(n-undecyl)indole-6-carboxylic acid by 2-(n-pentadecyl)indole-4-carboxylic acid, there was prepared n-butyl 2-(n-pentadecyl)indole-4-carboxylate, in the form of an off-white solid, m.p. 40°–42° C.

EXAMPLE 42

Compound NN

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-pentadecanamido)-3-methylbenzoic acid, there was prepared 2-(n-tetradecyl)indole-5-carboxylic acid, in the form of a buff solid, m.p. 117°–120° C.

By proceeding in a similar manner to that hereinbefore described in Example 5(i) for the preparation of 3-(n-decanamido)-4-methylbenzoic acid but replacing n-decanoyl chloride by n-pentadecanoyl chloride and 3-amino-4-methylbenzoic acid by 4-amino-3-methylbenzoic acid, there was prepared 4-(n-pentadecanamido)-3-methylbenzoic acid, in the form of a white solid, m.p. 198°–201° C., used in the preparation above.

EXAMPLE 43

Compound OO

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-heptadecanamido)-3-methylbenzoic acid, there was prepared 2-(n-hexadecyl)indole-5-carboxylic acid, in the form of a buff solid, m.p. 108°–110° C.

By proceeding in a similar manner to that hereinbefore described in Example 5(i) for the preparation of 3-(n-decanamido)-4-methylbenzoic acid but replacing n-decanoyl chloride by n-heptadecanoyl chloride and 3-amino-4-methylbenzoic acid by 4-amino-3-methylbenzoic acid, there was prepared 4-(n-heptadecanamido)-3-methylbenzoic acid, in the form of an off-white solid, m.p. 197°–200° C. used in the preparation above.

EXAMPLE 44

Compound PP

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4(n-eicosanamido)-3-methylbenzoic acid, there was prepared 2-(n-nonadecyl)indole-5-carboxylic acid, in the form of a white solid, m.p. 110°–111° C.

By proceeding in a similar manner to that hereinbefore described in Example 5(i) for the preparation of 3-(n-decanamido)-4-methylbenzoic acid but replacing n-decanoyl chloride by n-eicosanoyl chloride and 3-amino-4-methylbenzoic acid by 4-amino-3-methylbenzoic acid, there was prepared 4-(n-eicosanamido)-3-methylbenzoic acid, in the form of a white solid, m.p. 193°–196° C., used in the preparation above.

EXAMPLE 45

Compound QQ

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 4-(n-tetracosanamido)-3-methylbenzoic acid, there was prepared 2-(n-tricosyl)indole-5-carboxylic acid, in the form of a buff solid, m.p. 112°–114° C.

By proceeding in a similar manner to that hereinbefore described in Example 5(i) for the preparation of 3-(n-decanamido)-4-methylbenzoic acid but replacing n-decanoyl chloride by n-tetracosanoyl chloride and 3-amino-4-methylbenzoic acid by 4-amino-3-methylbenzoic acid, there was prepared 4-(n-tetracosanamido)-3-methylbenzoic acid, in the form of a buff solid, m.p. 184°–189° C., used in the preparation above.

EXAMPLE 46

Compound RR

By proceeding in a similar manner to that hereinbefore described in Example 1 for the preparation of 2-(n-pentadecyl)indole-6-carboxylic acid but replacing 3-(n-hexadecanamido)-4-methylbenzoic acid by (RS)-4-(2-methylundecanamido)-3-methylbenzoic acid, there was prepared (RS)-2-(1-methyldecyl)indole-5-carboxylic acid, in the form of a cream solid, m.p. 103°–106° C.

By proceeding in a similar manner to that hereinbefore described in Example 5(i) for the preparation of 3-(n-decanamido)-4-methylbenzoic acid but replacing n-decanoyl chloride by (RS)-2-methylundecanoyl chloride and 3-amino-4-methylbenzoic acid by 4-amino-3-methylbenzoic acid there was prepared (RS)-4-(2-methylundecanamido)-3-methylbenzoic acid, in the form of an off-white solid, m.p. 186°–190° C., used in the preparation above.

EXAMPLE 47

Compound SS

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-pentadecanamido)-4-methylbenzoic acid, there was prepared 2-(n-tetradecyl)indole-6-carboxylic acid, in the form of an off-white solid, m.p. 147°–150° C.

By proceeding in a similar manner to that hereinbefore described in Example 5(i) for the preparation of 3-(n-decanamido)-4-methylbenzoic acid but replacing n-decanoyl chloride by n-pentadecanoyl chloride, there was prepared 3-(n-pentadecanamido)-4-methylbenzoic acid, in the form of an off-white solid, m.p. 238°–241° C., used in the preparation above.

EXAMPLE 48

Compound TT

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-heptadecanamido)-4-methylbenzoic acid, there was prepared 2-(n-hexadecyl)indole-6-carboxylate acid, in the form of a yellow solid, m.p. 136°–140° C.

By proceeding in a similar manner to that hereinbefore described in Example 5(i) for the preparation of 3-(n-decanamido)-4-methylbenzoic acid but replacing n-decanoyl chloride by n-heptadecanoyl chloride, there was prepared 3-(n-heptadecanamido)-4-methylbenzoic acid, in the form of a white solid, m.p. 238°–240° C., used in the preparation above.

EXAMPLE 49

Compound UU

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 3-(n-heneicosanamido)-4-methylbenzoic acid, there was prepared 2-(n-eicosyl)indole-6-carboxylic acid, in the form of an off-white solid, m.p. 133°–135° C.

By proceeding in a similar manner to that hereinbefore described in Example 5(i) for the preparation of 3-(n-decanamido)-4-methylbenzoic acid but replacing n-decanoyl chloride by n-heneicosanoyl chloride there was prepared 3(n-heneicosanamido)-4-methylbenzoic acid, in the form of a white solid, m.p. 230°–234° C. used in the preparative above.

EXAMPLE 50

Compound VV

By proceeding in a similar manner to that hereinbefore described in Example 1 for the preparation of 2-(n-pentadecyl)indole-6-carboxylic acid but replacing 3-(n-hexadecanamido)-4-methylbenzoic acid by (RS)-3-(2-methylundecanamido)-4-methylbenzoic acid, there was prepared (RS)-2-(1-methyldecyl)indole-6-carboxylic acid, in the form of a cream solid, m.p. 81°–84° C.

By proceeding in a similar manner to that hereinbefore described in Example 5(i) for the preparation of 3-(n-decanamido)-4-methylbenzoic acid but replacing n-decanoyl chloride by (RS)-2-methylundecanoyl chloride, there was prepared (RS)-3-(2-methylundecanamido)-4-methylbenzoic acid, in the form of a white solid, m.p. 233°–236° C., used in the preparation above.

EXAMPLE 51

Compound WW

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 2-(n-decanamido)-3-methylbenzoic acid, there was prepared 2-(n-nonyl)indole-7-carboxylic acid, in the form of a white solid, m.p. 152°–155° C.

By proceeding in a similar manner to that hereinbefore described in Example 5(i) for the preparation of 3-(n-decanamido)-4-methylbenzoic acid but replacing 3-amino-4-methylbenzoic acid by 2-amino-3-methylbenzoic acid, there was prepared 2-(n-decanamido)-3-methylbenzoic acid, in the form of a white solid, m.p. 114°–116° C., used in the preparation above.

EXAMPLE 52

Compound XX

By proceeding in a similar manner to that hereinbefore described in Example 1 for the preparation of 2-(n-pentadecyl)indole-6-carboxylic acid but replacing 3-(n-hexadecanamido)-4-methylbenzoic acid by 2-(n-dodecanamido)-3-methylbenzoic acid, there was prepared 2-(n-undecyl)indole-7-carboxylic acid, in the form of a white solid, m.p. 155°–159° C.

By proceeding in a similar manner to that hereinbefore described in Example 5(i) for the preparation of 3-(n-decanamido)-4-methylbenzoic acid but replacing n-decanoyl chloride by n-dodecanoyl chloride and 3-amino-4-methylbenzoic acid by 2-amino-3-methylbenzoic acid, there was prepared 2-(n-dodecanamido)-3-methylbenzoic acid, in the form of a white solid, m.p. 114°–116° C., used in the preparation above.

EXAMPLE 53

Compound S

By proceeding in a similar manner to that hereinbefore described in Example 39 for the preparation of sodium 2-(n-pentadecyl)indole-6-carboxylate but replacing 2-(n-pentadecyl)indole-6-carboxylic acid by 2-(n-dodecyl)indole-6-carboxylic acid, there was prepared sodium 2-(n-dodecyl)indole-6-carboxylate hydrate in the form of colourless needles, m.p. greater than 340° C.

EXAMPLE 54

Compound L

By proceeding in a similar manner to that hereinbefore described in Example 39 for the preparation of sodium 2-(n-pentadecyl)indole-6-carboxylate but replacing 2-(n-pentadecyl)indole-6-carboxylic acid by 2-(n-nonyl)indole-6-carboxylic acid, there was prepared sodium 2-(n-nonyl)indole-6-carboxylate, in the form of colourless needles, m.p. greater than 340° C.

EXAMPLE 55

Compound G

By proceeding in a similar manner to that hereinbefore described in Example 39 for the preparation of sodium 2-(n-pentadecyl)indole-6-carboxylate but replacing 2-(n-pentadecyl)indole-6-carboxylic acid by 2-(n-pentadecyl)indole-5-carboxylic acid and ethanol by acetone, there was prepared sodium 2-(n-pentadecyl)indole-5-carboxylate, in the form of colourless needles, m.p. greater than 320° C.

EXAMPLE 56 Compound YY 2-(n-Undecyl)indole-5-carboxylic acid (45 g) was added to a mixture of tetrahydrofuran (250 ml), glacial acetic acid (50 ml) and perchloric acid (25 ml of strength 70% w/v). The mixture was hydrogenated over palladium on charcoal (5% w/w, 5 g) at room temperature and atmospheric pressure. When hydrogen uptake had ceased (after 6 hours), the mixture was filtered through diatomaceous earth, and the residue was washed with tetrahydrofuran (2×50 ml). The combined filtrates were adjusted to pH 4 by treatment with an aqueous solution of sodium hydroxide (strength 50% w/v). The mixture was diluted with water (200 ml) and was extracted with diethyl ether (3×200 ml). The diethyl ether solution was dried over magnesium sulphate and, on evaporation in vacuo gave a solid. The solid was dissolved in diethyl ether (100 ml) and the solution was treated with an excess of a solution of hydrogen chloride in ethanol (strength 38% w/v, 30 ml). The mixture was diluted with diethyl ether (1000 ml) and a solid was collected. The solid was recrystallised from isopropanol to give (RS)-2-(n-undecyl)-indoline-5-carboxylic acid hydrochloride (27.6 g), in the form of a white solid m.p. 175°–179° C. (with decomposition).

The corresponding parent indoline was prepared as follows:

(RS)-2-(n-undecyl)indoline-5-carboxylic acid hydrochloride (32.9 g) in ethanol (150 ml) containing sodium hydroxide (10 g) and water (38 ml) was stirred and refluxed for 1.5 hours. Glacial acetic acid (15 ml) was added to the hot solution and the mixture was cooled to 0° C. and then diluted with water (600 ml). The solid was collected and was recrystallized from methanol to give (RS)-2-(n-undecyl)indoline-5-carboxylic acid (25.7 g), in the form of a white solid, m.p. 99°-103° C.

By proceeding in a similar manner to that hereinbefore described in Example 18 for the preparation of sodium (RS)-2-(n-pentadecyl)indoline-6-carboxylate but replacing (RS)-2-(n-pentadecyl)indoline-6-carboxylic acid by (RS)-2-(n-undecyl)indoline-5-carboxylic acid there was prepared sodium (RS)-2-(n-undecyl)indoline-5-carboxylate, in the form of a buff solid, m.p. greater than 300° C.

EXAMPLE 57

Compound ZZ

A mixture of 2-(n-decyl)indole-6-carboxylic acid (62.5 g), perchloric acid (40 ml of strength 70% w/v) and glacial acetic acid (400 ml) were hydrogenated over palladium on charcoal (5% w/w, 8.0 g) at 80°-90° C. and atmospheric pressure. When hydrogen uptake had ceased (after 4 hours) the hot mixture was filtered and the residue was washed with hot (80° C.) glacial acetic acid (500 ml). The combined filtrates were concentrated in vacuo to 450 ml and were poured onto ice (1000 g). The mixture was adjusted to pH 9 by treatment with an aqueous solution of sodium hydroxide (strength 50% w/v) and was then adjusted to pH 4-5 with glacial acetic acid. The solid was collected, was washed with water (3×100 ml) and was dried. The solid was dissolved in boiling ethanol, treated with charcoal, and the solution was filtered. The filtrate was treated with an excess of a solution of hydrogen chloride in ethanol (90 ml of strength 37% w/v) and then the mixture was cooled and diluted with diethyl ether (750 ml). The solid was collected and treated as in Example 56 to give (RS)-2-(n-decyl)indoline-6-carboxylic acid (47.4 g), in the form of a buff solid, m.p. 123°-125° C.

By proceeding in a similar manner to that hereinbefore described in Example 18 for the preparation of (RS)-2-(n-pentadecyl)indoline-6-carboxylic acid hydrochloride but replacing (RS)-2-(n-pentadecyl)indoline-6-carboxylic acid by (RS)-2-(n-decyl)indoline-6-carboxylic acid there was prepared (RS)-2-(n-decyl)indoline-6-carboxylic acid hydrochloride, in the form of a white solid, m.p. 247°-250° C. with decomposition.

EXAMPLE 58

Compound AAA

Perchloric acid (3 ml) was added to a hot solution of 2-(n-pentadecyl)indole-5-carboxylic acid in glacial acetic acid (60 ml) and the mixture was hydrogenated at normal pressure using palladium on charcoal (5% w/w, 0.7 g) as catalyst. After 3.5 hours the hot mixture was filtered and the residue was washed with hot glacial acetic acid (30 ml). The pH of the combined filtrates was adjusted to 6 with 10% w/v sodium hydroxide solution. The mixture was extracted with diethyl ether (2×75 ml) and the ether solution was dried over magnesium sulphate. The solution was treated with a saturated solution of hydrogen chloride gas in ethanol to precipitate the hydrochloride. The solid was collected and recrystallised from isopropanol to give (RS)-2-(n-pentadecyl)indoline-5-carboxylic acid hydrochloride (5.6 g) as a white solid, m.p. 165°-170° C. with decomposition.

(RS)-2-(n-pentadecyl)indoline-5-carboxylic acid was prepared by treating a stirred suspension of hydrochloride salt (12.3 g) in water (100 ml) with a solution of sodium bicarbonate (3 g) in water (100 ml). The mixture was extracted with diethyl ether (2×100 ml) and the ether solution was dried over magnesium sulphate. Evaporation of the ether solution in vacuo gave (RS)-2-(n-pentadecyl)indoline-5-carboxylic acid (10.7 g) as a white solid m.p. 102°-104° C.

EXAMPLE 59

Compound ABB

By proceeding in a similar manner to that hereinbefore described in Example 57 for the preparation of (RS)-2-(n-decyl)indoline-6-carboxylic acid but replacing 2-(n-decyl)indole-6-carboxylic acid by 2-(n-heptyl)indole-5-carboxylic acid, there was prepared (RS)-2-(n-heptyl)indoline-5-carboxylic acid, in the form of a white solid, m.p. 109°-112° C.

EXAMPLE 60

Compound ACC

By proceeding in a similar manner to that hereinbefore described in Example 57 for the preparation of (RS)-2-(n-decyl)indoline-6-carboxylic acid but replacing 2-(n-decyl)indole-6-carboxylic acid by 2-(n-decyl)indole-5-carboxylic acid there was prepared (RS)-2-(n-decyl)indoline-5-carboxylic acid, in the form of a buff solid, m.p. 110°-112° C.

By proceeding in a similar manner to that hereinbefore described in Example 18 for the preparation of (RS)-2-(n-pentadecyl)indoline-6-carboxylic acid hydrochloride but replacing (RS)-2-(n-pentadecyl)-indoline-6-carboxylic acid by (RS)-2-(n-decyl)indoline-5-carboxylic acid, there was prepared (RS)-2-(n-decyl)indoline-5-carboxylic acid hydrochloride, in the form of a white solid, m.p. 182°-184° C. with decomposition.

EXAMPLE 61

Compound ADD

By proceeding in a similar manner to that hereinbefore described in Example 56 for the preparation of (RS)-2-(n-undecyl)indoline-5-carboxylic acid hydrochloride but replacing 2-(n-undecyl)indole-5-carboxylic acid by 2-(n-heptadecyl)indole-5-carboxylic acid there was prepared (RS)-2-(n-heptadecyl)indoline-5-carboxylic acid, in the form of a tan solid, m.p. 101°-103° C.

EXAMPLE 62

Compound AEE

By proceeding in a similar manner to that hereinbefore described in Example 57 for the preparation of (RS)-2-(n-decyl)indoline-6-carboxylic acid but replacing 2-(n-decyl)indole-6-carboxylic acid by 2-(n-heptyl)indole-6-carboxylic acid there was prepared (RS)-2-(n-heptyl)indoline-6-carboxylic acid, in the form of a cream solid, m.p. 139°-142° C.

By proceeding in a similar manner to that hereinbefore described in Example 18 for the preparation of (RS)-2-(n-pentadecyl)indoline-6-carboxylic acid hydrochloride but replacing (RS)-2-(n-pentadecyl)indoline-6-carboxylic acid by (RS)-2-(n-heptyl)indoline-6-carboxylic acid, there was prepared (RS)-2-(n-heptyl)indoline-6-carboxylic acid hydrochloride, in the form of a white solid, m.p. 255°-260° C. with decomposition.

EXAMPLE 63

Compound AFF

By proceeding in a similar manner to that hereinbefore described in Example 56 for the preparation of (RS)-2-(n-undecyl)indoline-5-carboxylic acid hydrochloride but replacing 2-(n-undecyl)indole-5-carboxylic acid by 2-(n-undecyl)indole-6-carboxylic acid there was prepared (RS)-2-(n-undecyl)indoline-6-carboxylic acid, in the form of a pale orange solid, m.p. 120°–23° C.

By proceeding in a similar manner to that hereinbefore described in Example 18 for the preparation of (RS)-2-(n-pentadecyl)indoline-6-carboxylic acid hydrochloride but replacing (RS)-2-(n-pentadecyl)indoline-6-carboxylic acid by (RS)-2-(n-undecyl)indoline-6-carboxylic acid there was prepared (RS)-2-(n-undecyl)indoline-6-carboxylic acid hydrochloride, in the form of a white solid, m.p. 232°–234° C. with decomposition.

By proceeding in a similar manner to that hereinbefore described in Example 18 for the preparation of sodium (RS)-2-(n-pentadecyl)indoline-6-carboxylate but replacing (RS)-2-(n-pentadecyl)indoline-6-carboxylic acid by (RS)-2-(n-undecyl)indoline-6-carboxylic acid there was prepared sodium (RS)-2-(n-undecyl)indoline-6-carboxylate, in the form of a white powder, m.p. greater than 300° C.

EXAMPLE 64

Compound AGG

By proceeding in a similar manner to that hereinbefore described in Example 56 for the preparation of (RS)-2-(n-undecyl)indoline-5-carboxylic acid hydrochloride but replacing 2-(n-undecyl)indole-5-carboxylic acid by 2-(n-tetradecyl)indole-6-carboxylic acid, there was prepared (RS)-2-(n-tetradecyl)indoline-6-carboxylic acid, in the form of a pale yellow solid, m.p. 117°–119° C.

By proceeding in a similar manner to that hereinbefore described in Example 18 for the preparation of (RS)-2-(n-pentadecyl)indoline-6-carboxylic acid hydrochloride but replacing (RS)-2-(n-pentadecyl)-indoline-6-carboxylic acid by (RS)-2-(n-tetradecyl)indoline-6-carboxylic acid, there was prepared (RS)-2-(n-tetradecyl)indoline-6-carboxylic acid hydrochloride, in the form of a white solid, m.p. 244°–250° C. with decomposition.

EXAMPLE 65

Compound AHH

By proceeding in a similar manner to that hereinbefore described in Example 33 for the preparation of ethyl 2-(n-dodecyl)indole-5-carboxylate but replacing 2-(n-dodecyl)indole-5-carboxylic acid by (RS)-2-(n-undecyl)indoline-6-carboxylic acid (prepared as described hereinbefore in Example 63), there was prepared (RS)-ethyl 2-(n-undecyl)indoline-6-carboxylate hydrochloride, in the form of a pale pink solid, m.p. 136°–138° C.

EXAMPLE 66

Compound AII

By proceeding in a similar manner to that hereinbefore described in Example 31 for the preparation of methyl 2-(n-undecyl)indole-6-carboxylate but replacing 2-(n-undecyl)-6-carboxylic acid by 2-(n-heptyl)indole-6-carboxylic acid, there was prepared methyl 2-(n-heptyl)indole-6-carboxylate, in the form of an off-white solid, m.p. 86°–89° C.

EXAMPLE 67

Compound AJJ

By proceeding in a similar manner to that hereinbefore described in Example 33 for the preparation of ethyl 2-(n-dodecyl)indole-5-carboxylate but replacing 2-(n-dodecyl)indole-5-carboxylic acid by 2-(n-heptyl)indole-6-carboxylic acid there was prepared ethyl 2-(n-heptyl)indole-6-carboxylate, in the form of a yellow solid, m.p. 83°–86° C.

EXAMPLE 68

Compound AKK

By proceeding in a similar manner to that hereinbefore described in Example 35 for the preparation of n-butyl 2-(n-undecyl)indole-6-carboxylate but replacing 2-(n-undecyl)indole-6-carboxylic acid by 2-(n-heptyl)indole-6-carboxylic acid, there was prepared n-butyl 2-(n-heptyl)indole-6-carboxylate, in the form of an off-white solid, m.p. 79°–83° C.

EXAMPLE 69

Compound ALL

By proceeding in a similar manner to that hereinbefore described in Example 35 for the preparation of n-butyl 2-(n-undecyl)indole-6-carboxylate but replacing 2-(n-undecyl)indole-6-carboxylic acid by 2-(n-dodecyl)indole-6-carboxylic acid, there was prepared n-butyl 2-(n-dodecyl)indole-6-carboxylate, in the form of an off-white solid, m.p. 72°–74° C.

EXAMPLE 70

Compound AMM

By proceeding in a similar manner to that hereinbefore described in Example 33 for the preparation of ethyl 2-(n-dodecyl)indole-5-carboxylate but replacing 2-(n-dodecyl)indole-5-carboxylic acid by 2-(n-tridecyl)indole-6-carboxylic acid, there was prepared ethyl 2-(n-tridecyl)indole-6-carboxylate, in the form of a buff solid, m.p. 83°–85° C.

EXAMPLE 71

Compound ANN

By proceeding in similar manner to that hereinbefore described in Example 31 for the preparation of methyl 2-(n-undecyl)indole-6-carboxylate but replacing 2-(n-undecyl)indole-6-carboxylic acid by 2-(n-pentadecyl)indole-6-carboxylic acid, there was prepared methyl 2-(n-pentadecyl)indole-6-carboxylate, in the form of a white solid, m.p. 90°–91° C.

EXAMPLE 72

Compound AOO

By proceeding in a similar manner to that hereinbefore described in Example 33 for the preparation of ethyl 2-(n-dodecyl)indole-5-carboxylate but replacing 2-(n-dodecyl)indole-5-carboxylic acid by 2-(n-pentadecyl)indole-6-carboxylic acid, there was prepared ethyl 2-(n-pentadecyl)indole-6-carboxylate, in the form of a white solid, m.p. 90°–92° C.

EXAMPLE 73

Compound APP

By proceeding in a similar manner to that hereinbefore described in Example 35 for the preparation of n-butyl 2-(n-undecyl)indole-6-carboxylate but replacing 2-(n-undecyl)indole-6-carboxylic acid by 2-(n-pentadecyl)indole-6-carboxylic acid, there was prepared n-butyl 2-(n-pentadecyl)indole-6-carboxylate, in the form of a white solid, m.p. 76°–79° C.

EXAMPLE 74

Compound AQQ

By proceeding in a similar manner to that hereinbefore described in Example 35 for the preparation of n-butyl 2-(n-undecyl)indole-6-carboxylate but replacing 2-(n-undecyl)indole-6-carboxylic acid by 2-(n-eicosyl)indole-6-carboxylic acid, there was prepared n-butyl 2-(n-eicosyl)indole-6-carboxylate, in the form of a white solid, m.p. 91°–94° C.

EXAMPLE 75

Compound ARR

By proceeding in a similar manner to that hereinbefore described in Example 35 for the preparation of n-butyl 2-(n-undecyl)indole-6-carboxylate but replacing 2-(n-undecyl)indole-6-carboxylic acid by 2-(n-heptyl)indole-5-carboxylic acid, there was prepared n-butyl 2-(n-heptyl)indole-5-carboxylate, in the form of an off-white solid, m.p. 71°–74° C.

EXAMPLE 76

Compound ASS

By proceeding in a similar manner to that hereinbefore described in Example 31 for the preparation of methyl 2-(n-undecyl)indole-6-carboxylate but replacing 2-(n-undecyl)indole-6-carboxylic acid by 2-(n-heptyl)indole-5-carboxylic acid, there was prepared methyl 2-(n-heptyl)indole-5-carboxylate, in the form of an off-white solid, m.p. 85°–88° C.

EXAMPLE 77

Compound ATT

By proceeding in a similar manner to that hereinbefore described in Example 31 for the preparation of methyl 2-(n-undecyl)indole-6-carboxylate but replacing 2-(n-undecyl)indole-6-carboxylic acid by 2-(n-undecyl)indole-5-carboxylic acid, there was prepared methyl 2-(n-undecyl)indole-5-carboxylate, in the form of an off-white solid, m.p. 78°–81° C.

EXAMPLE 78

Compound AUU

By proceeding in a similar manner to that hereinbefore described in Example 35 for the preparation of n-butyl 2-(n-undecyl)indole-6-carboxylate but replacing 2-(n-undecyl)indole-6-carboxylic acid by 2-(n-undecyl)indole-5-carboxylic acid, there was prepared n-butyl 2-(n-undecyl)indole-5-carboxylate, in the form of a buff solid, m.p. 68°–70° C.

EXAMPLE 79

Compound AVV

By proceeding in a similar manner to that hereinbefore described in Example 31 for the preparation of methyl 2-(n-undecyl)indole-6-carboxylate but replacing 2-(n-undecyl)indole-6-carboxylic acid by 2-(n-dodecyl)indole-5-carboxylic acid, there was prepared methyl 2-(n-dodecyl)indole-5-carboxylate, in the form of an off-white solid, m.p. 80°–83° C.

EXAMPLE 80

Compound AWW

By proceeding in a similar manner to that hereinbefore described in Example 31 for the preparation of methyl 2-(n-undecyl)indole-6-carboxylate but replacing 2-(n-undecyl)indole-6-carboxylic acid by 2-(n-heptadecyl)indole-5-carboxylic acid, there was prepared methyl 2-(n-heptadecyl)indole-5-carboxylate, in the form of an off-white solid, m.p. 95°–97° C.

EXAMPLE 81

Compound AXX

Sodium hydride (0.32 g of a 50% oil dispersion) was added to a stirred solution of (RS)-2-(n-decyl)indoline-6-carboxylic acid (2 g; prepared as described hereinbefore in Example 57) in dry dimethylformamide (50 ml). When the addition was complete, the mixture was warmed on the steam bath for 1 hour with stirring, and 3-chloro-1,2-propanediol (0.8 g) was added. The mixture was warmed on the steam bath for 20 hours with stirring. The solvent was then evaporated to dryness and the residue was dissolved in dichloromethane. The solution in dichloromethane was washed with water, dried over magnesium sulphate and filtered, and the solvent evaporated to dryness to give an oil which slowly solidified. This solid was washed with petroleum ether (b.p. 60°–80° C.), filtered off and dried in air to give (RS)(RS)-2,3-dihydroxyprop-1-yl 2-(n-decyl)indoline-6-carboxylate (1.5 g), in the form of an off-white powder m.p. 102°–110° C.

EXAMPLE 82

Compound BB

Raney nickel (5 g) was added to a solution of ethyl 2-(n-pentadecyl)-3-methylthioindole-5-carboxylate (0.5 g) in dioxan (25 ml) and the mixture was heated on a steam bath for 1 hour. The mixture was filtered hot and the filtrate was evaporated in vacuo to give a white solid. This solid was recrystallised from petroleum ether (b.p. 60°–80° C.) to give ethyl 2-(n-pentadecyl)indole-5-carboxylate (0.35 g), m.p. 89°–91° C.

Ethyl 2-(n-pentadecyl)-3-methylthioindole-5-carboxylate used as starting material was prepared as follows:

A solution of tert-butyl hypochlorite (5.4 g) in methylene chloride (30 ml) was added dropwise to a stirred solution of ethyl 4-aminobenzoate (8.3 g) in methylene chloride (100 ml) at −65° C. After 15 minutes, a solution of 1-methylthioheptadecan-2-one (15 g) in methylene chloride (60 ml) was added. The stirring at −65° C. was continued for 1 hour and a solution of triethylamine (5 g) in methylene chloride (20 ml) was then added. The reaction mixture was allowed to warm to room temperature. Water (50 ml) was added, and the organic layer was separated, dried over magnesium sulphate and evaporated in vacuo. The residue was dissolved in chloroform (20 ml) and chromatographed on a silica column (3.5 cm diameter×45 cm) using chloroform as the eluant. The crude ethyl 2-(n-pentadecyl)-3-methylthioindole-5-carboxylate (4.2 g) was obtained as an orange solid, m.p. 55°–60° C.

1-Methylthioheptadecan-2-one was synthesised as follows:

(i) A stirred mixture of 1-methylsulphinylheptadecan-2-one (10 g), water (100 ml), sodium metabisulphate (50 g) and dioxan (50 ml) was heated on a steam bath for 18 hours. The mixture was cooled to room temperature and extracted with diethyl ether (2×100 ml). The ether extract was dried over magnesium sulphate and was evaporated to give 1-methylthioheptadecan-2-one (5.7 g) as a white solid, m.p. 38°–40° C.

(ii) A solution of trifluoroacetic anhydride (1.68 g) in acetone (5 ml) was added to a stirred mixture of 1-methylsulphinylheptadecan-2-one (1.58 g) and sodium iodide (1.8 g) in acetone (10 ml) cooled in an ice bath. The mixture was stirred for a further 10 minutes and then evaporated. Water (50 ml) was added to the residue and the mixture was extracted with diethyl ether (2×40 ml). The ether extract was washed with a solution of sodium thiosulphate (3 g) in water (50 ml), dried over magnesium sulphate and evaporated to give 1-methylthioheptadecan-2-one (1.3 g), m.p. 40° C.

EXAMPLE 83

Compound G

A stirred mixture of 4-(n-hexadecanamido)-3-methylbenzoic acid (4 g), potassium tert-butoxide (4 g) and diethylaniline (10 ml) was refluxed for 3.5 hours. The fraction boiling at less than 200° C. during the reaction was collected. The reaction mixture was left to cool to room temperature and was then acidified with 10% w/v hydrochloric acid. The solid was filtered off, dried and recrystallized from toluene to give 2-(n-pentadecyl)indole-5-carboxylic acid (2.7 g), m.p. 108°–110° C.

EXAMPLE 84

Compound C

A mixture of 3-(n-dodecanamido)-4-methylbenzoic acid (4 g), potassium tert-butoxide (4 g) and diethylaniline (10 ml) was treated in a similar manner to that hereinbefore described in Example 83 to give 2-(n-undecyl)indole-6-carboxylic acid (2.6 g), m.p. 156°–158° C.

EXAMPLE 85

Compound AYY

A solution of borane in tetrahydrofuran (134 ml, of strength 1M) in portions (13×10 ml) was added during 20 minutes to a stirred solution of methyl 3-(n-dodecanoyl)indole-6-carboxylate (19.9 g) in a mixture of dry tetrahydrofuran (330 ml) and dry ethyl acetate (330 ml), the temperature of the reaction being maintained at 50° C. by external warming. The mixture was stirred and refluxed for 1.5 hours and then methanol (330 ml) was added to the refluxing mixture during 10 minutes. The mixture was refluxed for a further 30 minutes and water (50 ml) was added. The mixture was distilled at atmospheric pressure to remove the organic solvents to give a yellow residue. The residue was triturated with water (50 ml) to give a solid, which was collected and washed with water (100 ml). The solid was recrystallised from methanol (100 ml) (with treatment with charcoal) and then from toluene to give methyl 3-(n-dodecyl)-indole-6-carboxylate (10 g), in the form of a white solid, m.p. 85°–89° C.

(i) The methyl 3-(n-dodecanoyl)indole-6-carboxylate, used as starting material, was prepared as follows:

Phosphorus oxychloride (27.5 ml) was added dropwise during 20 minutes to stirred N,N-dimethyldodecanamide (84.9 g) at room temperature. The temperature of the mixture rose during the addition to 50° C. The mixture was stirred and heated at 90° C. for 15 minutes and then methyl indole-6-carboxylate (33.4 g) was added portionwise to the stirred mixture during 10 minutes, the temperature of the mixture being maintained at 90° C. during the addition. The mixture was then stirred for 2 hours at 90° C. and was then poured onto ice. The aqueous mixture was extracted with chloroform (3×300 ml) and the extract was dried over magnesium sulphate and was evaporated to give a red brown oil. The oil was dissolved in boiling methanol (100 ml), the solution was treated with charcoal and the solution was filtered and cooled (0° C.) to give methyl 3-(n-dodecanoyl)indole-6-carboxylate (26.7 g), in the form of a buff solid, m.p. 167°–169° C.

EXAMPLE 86

Compound AZZ

By proceeding in a similar manner to that hereinbefore described in Example 85 for the preparation of methyl 3-(n-dodecyl)indole-6-carboxylate but replacing methyl 3-(n-dodecanoyl)indole-6-carboxylate by methyl 3-(n-octanoyl)indole-6-carboxylate, there was prepared methyl 3-(n-octyl)indole-6-carboxylate, in the form of a white solid, m.p. 78°–79° C.

By proceeding in a similar manner to that hereinbefore described in Example 85(i) for the preparation of methyl 3-(n-dodecanoyl)indole-6-carboxylate but replacing N,N-dimethyldodecanamide by N,N-dimethyloctanamide, there was prepared methyl 3-(n-octanoyl)indole-6-carboxylate in the form of a white solid, m.p. 205°–208° C. after recrystallisation from glacial acetic acid, used in the preparation above.

EXAMPLE 87

Compound BAA

By proceeding in a similar manner to that hereinbefore described in Example 85 for the preparation of methyl 3-(n-dodecyl)indole-6-carboxylate but replacing methyl 3-(n-dodecanoyl)indole-6-carboxylate by methyl 3-(n-hexadecanoyl)indole-6-carboxylate, there was prepared methyl 3-(n-hexadecyl)indole-6-carboxylate in the form of a white solid, m.p. 89°–94° C. after recrystallization from methanol.

By proceeding in a similar manner to that hereinbefore described in Example 85(i) for the preparation of methyl 3-(n-dodecanoyl)indole-6-carboxylate but replacing N,N-dimethyldodecanamide by N,N-dimethylhexadecanamide, there was prepared methyl 3-(n-hexadecanoyl)indole-6-carboxylate in the form of a white solid, m.p. 156°–158° C. after recrystallization from ethyl acetate, used in the preparation above.

EXAMPLE 88

Compound BBB

By proceeding in a similar manner to that hereinbefore described in Example 85 for the preparation of methyl 3-(n-dodecyl)indole-6-carboxylate but replacing methyl 3-(n-dodecanoyl)indole-6-carboxylate by methyl 3-(n-octadecanoyl)indole-6-carboxylate, there was prepared methyl 3-(n-octadecyl)indole-6-carboxylate in the form of a white solid, m.p. 92°–94° C. after recrystallisation from methanol.

By proceeding in a similar manner to that hereinbefore described in Example 85(i) for the preparation of methyl 3-(n-dodecanoyl)indole-6-carboxylate but replacing N,N-dimethyldodecanamide by N,N-dimethyloctadecanamide, there was prepared methyl 3-(n-octadecanoyl)indole-6-carboxylate in the form of a cream solid, m.p. 153°–155° C. after recrystallization from ethyl acetate, used in the preparation above.

EXAMPLE 89

Compound BCC

By proceeding in a similar manner to that hereinbefore described in Example 85 for the preparation of methyl 3-(n-dodecyl)indole-6-carboxylate but replacing methyl 3-(n-dodecanoyl)indole-6-carboxylate by methyl 3-(n-hexadecanoyl)indole-5-carboxylate, there was prepared methyl 3-(n-hexadecyl)indole-5-carboxylate in the form of a white solid, m.p. 85°–87° C. after recrystallization from methanol.

By proceeding in a similar manner to that hereinbefore described in Example 85(i) for the preparation of methyl 3(n-dodecanoyl)indole-6-carboxylate but replacing methyl indole-6-carboxylate by methyl indole-5-carboxylate and N,N-dimethyldodecanamide by N,N-dimethylhexadecanamide, there was prepared methyl 3-(n-hexadecanoyl)indole-5-carboxylate in the form of a cream solid, m.p. 158°–160° C. after recrystallization from ethyl acetate, used in the preparation above.

EXAMPLE 90

Compound BDD

A solution of sodium hydroxide (15 g) in water (100 ml) was added dropwise during 30 minutes to a refluxing solution of methyl 3-(n-dodecyl)indole-6-carboxylate (12.8 g prepared as hereinbefore described in Example 85) in methanol (800 ml). The mixture was stirred and refluxed for 12 hours. The mixture was then concentrated to 500 ml volume and water (400 ml) was added. After cooling to 0° C., a solid was collected and was dissolved in hot glacial acetic acid (300 ml). The solution was then poured into water (800 ml) and a solid was collected, washed with water (4×100 ml) and dried at 60° C. Recrystallisation of the solid from methanol gave 3-(n-dodecyl)indole-6-carboxylic acid (9.0 g), in the form of a white solid, m.p. 181°–184° C.

EXAMPLE 91

Compound BEE

By proceeding in a similar manner to that hereinbefore described in Example 90 for the preparation of 3-(n-dodecyl)indole-6-carboxylic acid but replacing methyl 3-(n-dodecyl)indole-6-carboxylate by methyl 3-(n-octyl)indole-6-carboxylate, there was prepared 3-(n-octyl)indole-6-carboxylic acid in the form of a white solid, m.p. 195°–197° C. after recrystallisation from toluene.

EXAMPLE 92

Compound BFF

By proceeding in a similar manner to that hereinbefore described in Example 90 for the preparation of 3-(n-dodecyl)indole-6-carboxylic acid but replacing methyl 3-(n-dodecyl)indole-6-carboxylate by methyl 3-(n-hexadecyl)indole-6-carboxylate, there was prepared 3-(n-hexadecyl)indole-6-carboxylic acid in the form of a white solid, m.p. 174°–178° C. after recrystallisation from ethyl acetate:

EXAMPLE 93

Compound BGG

By proceeding in a similar manner to that hereinbefore described in Example 90 for the preparation of 3-(n-dodecyl)indole-6-carboxylic acid but replacing methyl 3-(n-dodecyl)indole-6-carboxylate by methyl 3-(n-octadecyl)indole-6-carboxylate, there was prepared 3-(n-octadecyl)indole-6-carboxylic acid in the form of a white solid, m.p. 172°–174° C. after recrystallisation from ethyl acetate.

EXAMPLE 94

Compound BHH

By proceeding in a similar manner to that hereinbefore described in Example 90 for the preparation of 3-(n-dodecyl)indole-6-carboxylic acid but replacing methyl 3-(n-dodecyl)indole-6-carboxylate by methyl 3-(n-hexadecyl)indole-5-carboxylate, there was prepared 3-(n-hexadecyl)indole-5-carboxylic acid in the form of an off-white solid, m.p. 114°–116° C. after recrystallisation from glacial acetic acid.

EXAMPLE 95

Compound BII

A mixture of (RS)-2-(n-undecyl)indoline-6-carboxylic acid (13.3 g), sodium hydroxide (13.3 g), water (40 ml), ethanol (160 ml) and methyl iodide (15 ml) was heated under reflux for 1 hour. Methyl iodide (5 ml) was added and the mixture was heated for 1 hour, then poured into water, and acidified with acetic acid. The product was collected and recrystallized from methanol to give (PS)-1-methyl-2-(n-undecyl)indoline-6-carboxylic acid (8.9 g), in the form of white needles, m.p. 121°–124° C.

EXAMPLE 96

Compound BJJ

A mixture of (RS)-2-(n-undecyl)indoline-5-carboxylic acid hydrochloride (6.8 g), sodium hydroxide (6.8 g), water (25 ml), ethanol (75 ml) and methyl iodide (10 ml) was heated under reflux for 1 hour. Methyl iodide (5 ml) was added and the mixture was heated for 30 minutes, then poured into water and acidified with acetic acid. The product was collected and recrystallised from methanol to give (RS)-1-methyl-2-(n-undecyl)indoline-5-carboxylic acid (3.0 g), in the form of white needles, m.p. 102°–104° C.

EXAMPLE 97

Compound BKK

Methyl 3-(n-octadecanoyl)indole-5-carboxylate (17.30 g) was suspended in glacial acetic acid (400 ml), containing perchloric acid (11 ml, 70% w/v), and was hydrogenated over palladium on charcoal (5% w/w, 15 g) at atmospheric pressure and at a temperature of 80°–90° C. The mixture was then hot filtered through diatomaceous earth and was poured into water (150 ml) to give an off-white solid. The solid was collected, washed with water (2×100 ml) and was dissolved in ethyl acetate (1000 ml). The ethyl acetate solution was washed with an aqueous solution of sodium carbonate (of strength 2N, 150 ml) and the organic layer was separated and was dried over magnesium sulfate. The organic solvent was removed in vacuo to give (RS)-methyl 3-(n-octadecyl)indoline-5-carboxylate in the form of an off-white solid, which was used without purification.

By proceeding in a similar manner to that hereinbefore described in Example 85(i) for the preparation of methyl 3-(n-dodecanoyl)indole-6-carboxylate but replacing N,N-dimethyldodecanamide by N,N-dimethyloctadecanamide and methyl indole-6-carboxylate by methyl indole-5-carboxylate, there was prepared methyl 3-(n-octadecanoyl)indole-5-carboxylate in the form of an off-white solid, used in the preparation above, without further purification.

EXAMPLE 98

Compound BLL

By proceeding in a similar manner to that hereinbefore described in Example 97 for the preparation of (RS)-methyl 3-(n-octadecyl)indoline-5-carboxylate but replacing methyl 3-(n-octadecanoyl)indole-5-carboxylate by methyl 3-(n-decanoyl)indole-5-carboxylate, there was prepared (RS)-methyl 3-(n-decyl)indoline-5-carboxylate in the form of an off-white solid, m.p. 53°–55° C. after recrystallisation from methanol.

By proceeding in a similar manner to that hereinbefore described in Example 85(i) for the preparation of methyl 3-(n-dodecanoyl)indole-6-carboxylate but replacing N,N-dimethyldodecanamide by N,N-dimethyldecanamide and methyl indole-6-carboxylate by methyl indole-5-carboxylate, there was prepared methyl 3-(n-decanoyl)indole-5-carboxylate in the form of a white solid, m.p. 173°–175° C. after recrystallisation from methanol, used in the preparation above.

EXAMPLE 99

Compound BMM

By proceeding in a similar manner to that hereinbefore described in Example 97 for the preparation of (RS)-methyl 3-(n-octadecyl)indoline-5-carboxylate but replacing methyl 3-(n-octadecanoyl)indole-5-carboxylate by methyl 3-(n-octanoyl)indole-5-carboxylate, there was prepared (RS)-methyl 3-(n-octyl)indoline-5-carboxylate in the form of a solid, having a low melting point.

By proceeding in a similar manner to that hereinbefore described in Example 85(i) for the preparation of methyl 3-(n-dodecanoyl)indole-6-carboxylate but replacing N,N-dimethyldodecanamide by N,N-dimethyloctanamide and methyl indole-6-carboxylate by methyl indole-5-carboxylate, there was prepared methyl 3-(n-octanoyl)indole-5-carboxylate in the form of a solid, m.p. 102°–105° C. after recrystallisation from ethyl acetate, used in the preparation above.

EXAMPLE 100

Compound BNN

By proceeding in a similar manner to that hereinbefore described in Example 97 for the preparation of (RS)-methyl 3-(n-octadecyl)indoline-5-carboxylate but replacing methyl 3-(n-octadecanoyl)indole-5-carboxylate by methyl 3-(n-hexadecanoyl)indole-5-carboxylate, there was prepared (RS)-methyl 3-(hexadecyl)indoline-5-carboxylate in the form of an off-white solid, m.p. 69°–71° C.

By proceeding in a similar manner to that hereinbefore described in Example 85(i) for the preparation of methyl 3-(n-dodecanoyl)indole-6-carboxylate but replacing N,N-dimethyldodecanamide by N,N-dimethylhexadecanamide and methyl indole-6-carboxylate by methyl indole-5-carboxylate, there was prepared methyl 3-(n-hexadecanoyl)indole-5-carboxylate in the form of a solid, m.p. 158°–160° C. after recrystallisation from ethyl acetate, used in the preparation above.

EXAMPLE 101

Compound BOO (RS)-Methyl 3-(n-octadecyl)indoline-5-carboxylate (13.6 g) in ethanol (380 ml), containing potassium hydroxide (2.7 g) and water (50 ml), was refluxed with stirring for 24 hours. The solvent was removed in vacuo to give an off-white solid. The solid was dissolved in water, and the solution treated with charcoal and filtered through diatomaceous earth. Glacial acetic acid (50 ml) was slowly added to the stirred solution and an off-white solid was collected, which was recrystallised from ethyl acetate to give (RS)-3-(n-octadecyl)indoline-5-carboxylic acid (9.1 g), in the form of a white solid, m.p. 84°–87° C.

EXAMPLE 102

Compound BPP

By proceeding in a similar manner to that hereinbefore described in Example 101 for the preparation of (RS)-3-(n-octadecyl)indoline-5-carboxylic acid but replacing (RS)-methyl 3-(n-octadecyl)indoline-5-carboxylate by (RS)-methyl 3-(n-decyl)indoline-5-carboxylate, there was prepared (RS)-3-(n-decyl)indoline-5-carboxylic acid in the form of a cream solid, m.p. 88°–90° C. after recrystallisation from petroleum ether (b.p. 60°–80° C.).

EXAMPLE 103

Compound BQQ

By proceeding in a similar manner to that hereinbefore described in Example 101 for the preparation of (RS)-3-(n-octadecyl)indoline-5-carboxylic acid but replacing (RS)-methyl 3-(n-octadecyl)indoline-5-carboxylate by (RS)-methyl 3-(n-octyl)indoline-5-carboxylate, there was prepared (RS)-3-(n-octyl)indoline-5-carboxylic acid in the form of a white solid, m.p. 128°–130° C. after recrystallisation from ethyl acetate.

EXAMPLE 104

Compound BRR

By proceeding in a similar manner to that hereinbefore described in Example 101 for the preparation of (RS)-3-(n-octadecyl)indoline-5-carboxylic acid but replacing (RS)-methyl 3-(n-octadecyl)indoline-5-carboxylate by (RS)-methyl 3-(n-hexadecyl)indoline-5-carboxylate, there was prepared (RS)-3-(n-hexadecyl)indoline-5-carboxylic acid in the form of a white solid, m.p. 78°–80° C. after recrystallisation from petroleum ether (b.p. 40°–60° C.).

EXAMPLE 105

Compound BRR

The free base (8.7 g; prepared as hereinbefore described in Example 104) was dissolved in diethyl ether (200 ml) and the solution was filtered through diatomaceous earth. The solution was treated with aqueous hydrochloric acid (3 ml, of strength 36.5% w/v) and the precipitated solid was collected. The solid was recrystallised from ethyl acetate to give (RS)-3-(n-hexadecyl)indoline-5-carboxylic acid hydrochloride (7.4 g), in the form of a white solid, m.p. 141°–143° C.

EXAMPLE 106

Compound BSS (RS)-3-(n-Octadecyl)indoline-5-carboxylic acid (2.0 g) in mesitylene (20 ml) was treated with palladium on charcoal (5% w/w, 0.15 g) and the mixture was refluxed for 2 hours. The catalyst was removed by hot filtration and the solvent was evaporated in vacuo to give a solid. The solid was recrystallised from methanol to give 3-(n-octadecyl)indole-5-carboxylic acid (1.10 g) in the form of a buff solid (m.p. 110°–112° C.).

EXAMPLE 107

Compound BTT

By proceeding in a similar manner to that hereinbefore described in Example 106 for the preparation of 3-(n-octadecyl)indole-5-carboxylic acid but replacing (RS)-3-(n-octadecyl)indoline-5-carboxylic acid by (RS)-3-(n-octyl)indoline-5-carboxylic acid, there was prepared 3-(n-octyl)indole-5-carboxylic acid in the form of an off-white solid, m.p. 151°–154° C.

EXAMPLE 108

Compound BUU

By proceeding in a similar manner to that hereinbefore described in Example 97 for the preparation of (RS)-methyl 3-(n-octadecyl)indoline-5-carboxylate but replacing methyl 3-(n-octadecanoyl)indole-5-carboxylate by methyl 3-(n-undecanoyl)indole-6-carboxylate, there was prepared (RS)-methyl 3-(n-undecyl)indoline-6-carboxylate in the form of a white solid.

By proceeding in a similar manner to that hereinbefore described in Example 85(i) for the preparation of methyl 3-(n-dodecanoyl)indole-6-carboxylate but replacing N,N-dimethyldodecanamide by N,N-dimethylundecanamide there was prepared methyl 3-(n-undecanoyl)indole-6-carboxylate in the form of a white solid, m.p. 173°–176° C. after recrystallisation from ethyl acetate, used in the preparation above.

EXAMPLE 109

Compound BVV

By proceeding in a similar manner to that hereinbefore described in Example 97 for the preparation of (RS)-methyl 3-(n-octadecyl)indoline-5-carboxylate but replacing methyl 3-(n-octadecanoyl)indole-5-carboxylate by methyl 3-(n-decanoyl)indole-6-carboxylate, there was prepared (RS)-methyl 3-(n-decyl)indoline-6-carboxylate in the form of a white solid, m.p. 62°–65° C. after recrystallisation from methanol.

By proceeding in a similar manner to that hereinbefore described in Example 85(i) for the preparation of methyl 3-(n-dodecanoyl)indole-6-carboxylate but replacing N,N-dimethyldodecanamide by N,N-dimethyldecanamide, there was prepared methyl 3-(n-decanoyl)indole-6-carboxylate in the form of a white solid, m.p. 172°–173° C. after recrystallisation from ethyl acetate, used in the preparation above.

EXAMPLE 110

Compound BWW

By proceeding in a similar manner to that hereinbefore described in Example 97 for the preparation of (RS)-methyl 3-(n-octadecyl)indoline-5-carboxylate but replacing methyl 3-(n-octadecanoyl)indole-5-carboxylate by methyl 3-(n-pentadecanoyl)indole-6-carboxylate, there was prepared (RS)-methyl 3-(n-pentadecyl)indoline-6-carboxylate in the form of an off-white solid, m.p. 90°–92° C. after recrystallisation from methanol.

By proceeding in a similar manner to that hereinbefore described in Example 85(i) for the preparation of methyl 3-(n-dodecanoyl)indole-6-carboxylate but replacing N,N-dimethyldodecanamide by N,N-dimethylpentadecanamide, there was prepared methyl 3-(n-pentadecanoyl)-indole-6-carboxylate in the form of an off-white solid, m.p. 154°–156° C. after recrystallisation from ethyl acetate, used in the preparation above.

EXAMPLE 111

Compound BXX (RS)-Methyl 3-(n-undecyl)indoline-6-carboxylate (12.4 g) in ethanol (350 ml), containing potassium hydroxide (3.33 g) and water (45 ml), was stirred and refluxed for 24 hours. The solvent was removed in vacuo to give an off-white solid. The solid was dissolved in water, and the solution was treated with charcoal and filtered through diatomaceous earth. Glacial acetic acid (50 ml) was slowly added to the stirred solution and an off-white solid was collected and recrystallised from ethyl acetate to give (RS)-3-(n-undecyl)indoline-6-carboxylic acid (11.9 g), in the form of a white solid, m.p. 107°–111° C.

EXAMPLE 112

Compound BYY

By proceeding in a similar manner to that hereinbefore described in Example 111 for the preparation of (RS)-3-(n-undecyl)indoline-6-carboxylic acid but replacing (RS)-methyl 3-(n-undecyl)indoline-6-carboxylate by (RS)-methyl 3-(n-decyl)indoline-6-carboxylate, there was prepared (RS)-3-(n-decyl)indoline-6-carboxylic acid in the form of a white solid, m.p. 115°–117° C. after recrystallisation from ethyl acetate.

EXAMPLE 113

Compound BZZ

By proceeding in a similar manner to that hereinbefore described in Example 111 for the preparation of (RS)-3-(n-undecyl)indoline-6-carboxylic acid but replacing (RS)-methyl 3-(n-undecyl)indoline-6-carboxylate by (RS)-methyl 3-(n-pentadecyl)indoline-6-carboxylate, there was prepared (RS)-3-(n-pentadecyl)indoline-6-carboxylic acid in the form of an off-white solid, m.p. 105°–109° C.

EXAMPLE 114

Compound CAA 3-(n-Dodecyl)indole-6-carboxylic acid (16.1 g) in suspension in glacial acetic acid (200 ml), containing perchloric acid (12.2 ml; of strength (70% w/v) was hydrogenated over palladium on charcoal (1.8 g of 5% w/w) at atmospheric pressure and at a temperature of 80°–90° C. The mixture was then hot filtered through diatomaceous earth and was poured into water (1500 ml) to give an off-white solid. The solid was collected, washed with water (2×100 ml) and was dissolved in ethyl acetate (1000 ml). The ethyl acetate solution was washed with an aqueous solution of sodium carbonate (of strength 2N, 150 ml) and the organic layer was separated and was dried over magnesium sulphate. The organic solvent was removed in vacuo to give (RS)-3-(n-dodecyl)indoline-6-carboxylic acid (7.9 g), in the form of a white solid (m.p. 100°–102° C.).

EXAMPLE 115

Compound CBB 3-(n-Octadecanoyl)indole-6-carboxylic acid (20.5 g) in glacial acetic acid (300 ml), containing perchloric acid (13 ml, of strength 70% w/v), was hydrogenated over palladium on charcoal (3 g of 5% w/w) at atmospheric pressure and at a temperature of 80°–90° C. The mixture was then hot filtered through diatomaceous earth and was poured into water (1500 ml) to give an off-white solid. The solid was collected, washed with water (2×100 ml) and was dissolved in ethyl acetate (100 ml). The ethyl acetate solution was washed with an aqueous solution of sodium carbonate (of strength 2N, 150 ml) and the organic layer was separated and was dried over magnesium sulphate. The organic solvent was removed in vacuo to give (RS)-3-(n-octadecyl)indoline-6-carboxylic acid (8.5 g), in the form of an off-white solid, m.p. 112°–114° C.

(i) The 3-(n-octadecanoyl)indole-6-carboxylic acid used as starting material was prepared as follows:

Methyl 3-(n-octadecanoyl)indole-6-carboxylate (35.2 g) in methanol (1620 ml), containing sodium hydroxide (32 g) and water (49 ml), was stirred and refluxed for 2 hours. The solution was cooled to room temperature and the solid was collected. The solid was suspended in water (500 ml) and aqueous hydrochloric acid (20 ml, of strength 36% w/v) was added to the suspension with rapid stirring. The solid was collected and was recrystallised from glacial acetic acid to give 3-(n-octadecanoyl)indole-6-carboxylic acid (28 g), in the form of a white solid, m.p. 268°–270° C.

EXAMPLE 116

Compound CCC 3-(n-Octanoyl)indole-6-carboxylic acid (39.4 g) in glacial acetic acid (860 ml), containing perchloric acid (37 ml, of strength 70% w/v), was hydrogenated over palladium on charcoal (17 g of 5% w/w) at atmospheric pressure and at a temperature between 80°–90° C. The catalyst was removed by hot filtration through diatomaceous earth and on cooling a solid separated which was collected. The solid was washed with diethyl ether (2×100 ml) and was dissolved in ethyl acetate. The ethyl acetate solution was washed with an aqueous solution of sodium carbonate (2×100 ml of strength 2N) and was dried over magnesium sulphate and on evaporation in vacuo gave an off-white solid. The solid was dissolved in ethyl acetate (200 ml) and hydrogen chloride gas was bubbled through the solution. The resulting solid was collected and was washed with diethyl ether (2×200 ml) to give (RS)-3-(n-octyl)indoline-6-carboxylic acid hydrochloride (14.5 g), in the form of an off-white solid, m.p. 233°–234° C. with decomposition.

By proceeding in a similar manner to that hereinbefore described in Example 115(i) for the preparation of 3-(n-octadecanoyl)indole-6-carboxylic acid but replacing methyl 3-(n-octadecanoyl)indole-6-carboxylate by methyl 3-(n-octanoyl)indole-6-carboxylate, there was prepared 3-(n-octanoyl)indole-6-carboxylic acid in the form of a white solid, m.p. 283°–286° C. after recrystallisation from glacial acetic acid, used in the preparation above.

EXAMPLE 117

Compound CDD

By proceeding in a similar manner to that hereinbefore described in Example 116 for the preparation of (RS)-3-(n-octyl)indoline-6-carboxylic acid hydrochloride but replacing 3-(n-octanoyl)indole-6-carboxylic acid by 3-(n-hexadecanoyl)indole-6-carboxylic acid, there was prepared (RS)-3-(n-hexadecyl)-indoline-6-carboxylic acid hydrochloride in the form of a white solid, m.p. 204°–207° C.

By proceeding in a similar manner to that hereinbefore described in Example 115(i) for the preparation of 3-(n-octadecanoyl)indole-6-carboxylic acid but replacing methyl 3-(n-octadecanoyl)indole-6-carboxylate by methyl 3-(n-hexadecanoyl)indole-6-carboxylate, there was prepared 3-(n-hexadecanoyl)-indole-6-carboxylic acid in the form of a white solid, m.p. 273°–275° C. after recrystallisation from glacial acetic acid, used in the preparation above.

EXAMPLE 118

Compound CEE (RS)-3-(n-Octyl)indoline-6-carboxylic acid hydrochloride (7.5 g) in methanol (500 ml), containing hydrochloric acid (50 ml, of strength 36% w/v), was refluxed for 18 hours. The solvent was removed in vacuo and water (100 ml) was added to the residue to give a solid, which was collected, washed with water (2×200 ml) and dried. The solid was dissolved in dichloromethane and was washed with an aqueous solution of sodium bicarbonate (100 ml of strength 2% w/v) and then water (100 ml) and was dried over sodium sulphate. The solvent was removed in vacuo to give a pale yellow oil, which solidified. The solid was recrystallised from a mixture (4:1) of methanol and water to give (RS)-methyl 3-(n-octyl)indoline-6-carboxylate (4.8 g), in the form of a white solid, m.p. 57°–60° C.

EXAMPLE 119

Compound CFF

By proceeding in a similar manner to that hereinbefore described in Example 118 for the preparation of (RS)-methyl 3-(n-octyl)indoline-6-carboxylate but replacing (RS)-3-(n-octyl)indoline-6-carboxylic acid by (RS)-3-(n-hexadecyl)indoline-6-carboxylic acid there was prepared (RS)-methyl 3-(n-hexadecyl)indoline-6-carboxylate, in the form of an off-white solid, m.p. 76°–77° C.

EXAMPLE 120

Compound JJ

A mixture of [4-methoxycarbonyl-2-(n-dodecanamido)benzyl]triphenylphosphonium bromide (23.8 g) and potassium tert.-butoxide (3.9 g) were added to dry toluene (680 ml). The stirred mixture was heated to reflux for 15 minutes and cooled to room temperature. Ethyl acetate (1.5 liter) and saturated brine (750 ml) were added; the mixture was shaken and the organic phase separated. The organic extract was dried over magnesium sulphate and was evaporated in vacuo to give an oil. The oil was purified by chromatography on a silica column using chloroform as eluant to give a crude solid which was recrystallised from methanol to give methyl 2-(n-undecyl)indole-6-carboxylate (4.1 g) as an off-white solid, m.p. 83°–85° C.

The [4-methoxycarbonyl-2-(n-dodecanamido)-benzyl]triphenylphosphonium bromide, used as starting material, was prepared as follows:

n-Dodecanoyl chloride (9.9 g) was added dropwise to a stirred suspension of (2-amino-4-methoxycarbonylbenzyl)triphenylphosphonium bromide (22.9 g) in dry dimethylformamide (225 ml) and stirring continued for 3 hours. The resulting solution was evaporated in vacuo to give an orangebrown oil which on treatment with water gave a solid. The solid was collected, washed with water, dried, washed with diethyl ether and collected to give [4-methoxycarbonyl-2-(n-dodecanamido)benzyl]triphenylphosphonium bromide (22.9 g) in the form of a pale yellow solid, m.p. 142°–145° C.

EXAMPLE 121

Compound CGG (RS)-2-(n-Tetradecyl)indoline-6-carboxylic acid (10.5 g) and sodium hydroxide (5.0 g) were refluxed together in a mixture of water (30 ml) and methanol (70 ml) for 1.5 hours, then methyl iodide (5 ml) was added. Water (30 ml) was added and the mixture was refluxed for 1 hour. The mixture was filtered, and the filtrate was diluted with water and acidified with acetic acid. The product was collected and recrystallised from a mixture of methanol and ethanol to give (RS)-1-methyl-2-(n-tetradecyl)indoline-6-carboxylic acid (7.0 g) in the form of off-white crystals, m.p. 115°–118° C.

EXAMPLE 122

Compound CHH and its methyl ester

Potassium hydroxide (9.0 g) was added to a solution of 2-(n-undecyl)indole-6-carboxylic acid (22.1 g) in dimethylsulphoxide (100 ml) and water (5 ml), and the mixture was stirred and warmed on a steam bath to give a suspension. After 15 minutes the suspension was removed from the steam bath, methyl iodide (15 ml) was added, and the mixture was stirred for 2 hours with occasional warming. Methyl iodide (10 ml) was added and the mixture was stirred for 1 hour. The mixture was left to cool overnight and was then poured into water and acidified with 2N hydrochloric acid. The product was collected and washed. This product was then added to a mixture of ethanol (150 ml), water (50 ml), and sodium hydroxide (6.5 g), and the mixture was heated under reflux for 1 hour and then poured into water containing acetic acid (50 ml). The product was twice recrystallised from ethanol to give 1-methyl-2-(n-undecyl)indole-6-carboxylic acid (9.6 g), in the form of a white powder, m.p. 165°–168° C.

EXAMPLE 123

Compound CII and its methyl ester

Potassium hydroxide (16.5 g) was warmed in dry dimethylsulphoxide (150 ml) with stirring for 10 minutes. Water (7 ml) was added followed, after 5 minutes, by 2-(n-pentadecyl)indole-5-carboxylic acid (27.0 g). The mixture was cooled to room temperature and methyl iodide (15 ml) was added, producing an exothermic reaction. The mixture was stirred without heating for 1 hour, then poured into water (approx. 500 ml) containing concentrated hydrochloric acid (40 ml). The product was collected, washed with water, dissolved in a mixture of chloroform, diethyl ether and tetrahydrofuran, and the solution was dried over sodium sulphate. The solvent was evaporated in vacuo and the residue was recrystallised from toluene. The resulting crystals were dried by suction to give a solid (11.7 g) in the form of needles, m.p. 77°–79° C.

This solid (methyl ester of compound CII) was heated under reflux in ethanol (100 ml) and water (20 ml) with sodium hydroxide (2.0 g) for 2 hours. The hot solution was acidified with acetic acid, the product was filtered off, washed with water, ethanol, and petroleum ether (b.p. 40°–60° C.), and recrystallised from toluene to give 1-methyl-2-(n-pentadecyl)indole-5-carboxylic acid (10.0 g), in the form of a white powder, m.p. 127°–128° C.

EXAMPLE 124

Compound CJJ

By proceeding in a similar manner to that hereinbefore described in Example 1 for the preparation of 2-(n-pentadecyl)indole-6-carboxylic acid but replacing 3-(n-hexadecanamido)-4-methylbenzoic acid by (RS)-3-(2-methyloctadecanamido)-4-methylbenzoic acid, there was prepared (RS)-2-(1-methylheptadecyl)indole-6-carboxylic acid, in the form of a buff solid, m.p. 84°–88° C.

By proceeding in a similar manner to that hereinbefore described in Example 5(i) for the preparation of 3-(n-decanamido)-4-methylbenzoic acid but replacing n-decanoyl chloride by (RS)-2-methyloctadecanoyl chloride, there was prepared (RS)-3-(2-methyloctadecanamido)-4-methylbenzoic acid in the form of colourless needles, m.p. 220°–223° C. after recrystallisation from isopropanol, used in the preparation above.

EXAMPLE 125

Compound CKK

By proceeding in a similar manner to that hereinbefore described in Example 1 for the preparation of 2-(n-pentadecyl)indole-6-carboxylic acid but replacing 3-(n-hexadecanamido)-4-methylbenzoic acid by (RS)-4-(2-methylocatadecanamido)-3-methylbenzoic acid, there was prepared (RS)-2-(1-methylheptadecyl)-indole-5-carboxylic acid, in the form of an off-white solid, m.p. 68°–72° C.

By proceeding in a similar manner to that hereinbefore described in Example 5(i) for the preparation of 3-(n-decanamido)-4-methylbenzoic acid but replacing n-decanoyl chloride by (RS)-2-methyl-octadecanoyl-chloride and 3-amino-4-methylbenzoic acid by 4-amino-3-methylbenzoic acid, there was prepared (RS)-4-(2-methyloctadecanamido)-3-methylbenzoic acid, in the form of a colourless solid, m.p. 193°–195° C. after recrystallisation from isopropanol, used in the preparation above.

EXAMPLE 126

Compound CLL

By proceeding in a similar manner to that hereinbefore described in Example 57 for the preparation of (RS)-2-(n-decyl)indoline-6-carboxylic acid but replacing 2-(n-decyl)indole-6-carboxylic acid by (RS)-2-(1-methylheptadecyl)indole-6-carboxylic acid, there was prepared (RS)(RS)-2-(1-methylheptadecyl)-indoline-6-carboxylic acid, in the form of a buff solid, m.p. 80°–86° C.

EXAMPLE 127

Compound CMM

By proceeding in a similar manner to that hereinbefore described in Example 57 for the preparation of (RS)-2-(n-decyl)-indoline-6-carboxylic acid but replacing 2-(n-decyl)indole-6-carboxylic acid by (RS)-2-(1-methylheptadecyl)indole-5-carboxylic acid, there was prepared d(RS)(RS)-2-(1-methylheptadecyl)-indoline-5-carboxylic acid, in the form of a buff solid, m.p. 69°–76° C.

EXAMPLE 128

Compound CNN

With external steam heating, a mixture of methyl 3-formyl-2-(n-undecyl)indole-6-carboxylate (20.0 g) and palladium on charcoal (5% w/w, 4.0 g) in glacial acetic acid (150 ml) and perchloric acid (72% w/v, 15 ml) was shaken under hydrogen. When the uptake stopped, the mixture was filtered, the residue was washed with hot acetic acid (100 ml) and the filtrate was concentrated in vacuo to about 50 ml. This mixture was diluted with ethanol (200 ml), 50% w/v aqueous sodium hydroxide (100 ml) was added, followed by water (200 ml), and the mixture was refluxed for 2 hours. The hot solution was filtered, and the filtrate was poured into cold water (1500 ml). Acetic acid was added until pH 5, and the product was collected and recrystallised from methanol to yield 2(RS),3(RS)-2-(n-undecyl)-3-methylindoline-6-carboxylic acid (13.7 g), in the form of buff needles, m.p. 107°–110° C.

Methyl 3-formyl-2-(n-undecyl)indole-6-carboxylate, used as starting material, was prepared as follows:

A solution of phosphorus oxychloride (20 ml) in dimethylformamide (80 ml) was added to a solution of methyl 2-(n-undecyl)indole-6-carboxylate (58.3 g) in dimethylformamide (250 ml) and the mixture was stirred at a temperature of 55°–90° C. for 2 hours. After cooling, the mixture was poured into rapidly stirred water. Aqueous sodium hydroxide (50% w/v) was added until pH 12, the mixture was stirred for 10 minutes, and then glacial acetic acid was added to pH 5. The mixture was stirred until the gummy product solidified. The solid was then collected and recrystallised from ethanol to give methyl 3-formyl-2-(n-undecyl)indole-6-carboxylate (52.5 g), in the form of a buff powder, m.p. 147°–149° C.

EXAMPLE 129

Compound COO

By proceeding in a similar manner to that hereinbefore described in Example 128 for the preparation of 2(RS),3(RS)-2-(n-undecyl)-3-methyl-indoline-6-carboxylic acid but replacing methyl 3-formyl-2-(n-undecyl)indole-6-carboxylate by methyl 3-formyl-2-(n-undecyl)indole-5-carboxylate, there was prepared 2(RS),3(RS)-2-(n-undecyl)-3-methylindoline-5-carboxylic acid, in the form of an off-white solid, m.p. 102°–105° C.

Methyl 3-formyl-2-(n-undecyl)indole-5-carboxylate, used as starting material, was prepared as follows:

A solution of phosphorus oxychloride (21.5 ml) in dimethylformamide (80 ml) was added to a solution of methyl 2-(n-undecyl)indole-5-carboxylate (36.9 g) in dimethylformamide (320 ml) and the mixture was stirred at a temperature of 60°–70° C. for 2 hours. After cooling the mixture was poured into water (500 ml). An aqueous solution of sodium hydroxide (50% w/v) was added to the mixture to adjust the pH to 12. Glacial acetic acid was then added to the stirred mixture to readjust the pH to 5. The resultant solid was collected and on recrystallisation from ethanol gave methyl 3-formyl-2-(n-undecyl)indole-5-carboxylate (34.8 g), m.p. 162°–165° C.

EXAMPLE 130

Compound CPP

A mixture of 2(RS),3(RS)-2-(n-undecyl)-3-methylindoline-6-carboxylic acid (23.0 g) and palladium on charcoal (5% w/w; 3.0 g) was stirred in refluxing mesitylene (150 ml) for 3.5 hours. The hot suspension was filtered, the residue was washed with hot mesitylene (50 ml) and the filtrate was set aside to cool. The product crystallised directly from the filtrate yielding 2-(n-undecyl)-3-methylindole-6-carboxylic acid (20.6 g) in the form of lustrous, white plates, m.p. 153°–156° C.

EXAMPLE 131

Compound CQQ

By proceeding in a similar manner to that hereinbefore described in Example 130 for the preparation of 2-(n-undecyl)-3-methylindole-6-carboxylic acid but replacing 2(RS),3(RS)-2-(n-undecyl)-3-methyl-indoline-6-carboxylic acid by 2(RS),3(RS)-2-(n-undecyl)-3-methylindoline-5-carboxylic acid, there was prepared 2-(n-undecyl)-3-methylindole-5-carboxylic acid in the form of a white solid, m.p. 102°–105° C.

EXAMPLE 132

Compound CRR

A mixture containing 2-(n-undecyl)indole-4-carboxylic acid (25.8 g), palladium on charcoal (5% w/w, 5.2 g), 72% w/v aqueous perchloric acid (26 ml) and glacial acetic acid (200 ml) was heated by external application of steam while being shaken under an atmosphere of hydrogen. When the required hydrogen had been taken up, the hot mixture was filtered through diatomaceous earth, the residue was washed with fresh hot glacial acetic acid (200 ml), and the combined filtrates were concentrated in vacuo to about 75 ml. The residue was poured onto crushed ice and water, and 50% w/v aqueous sodium hydroxide was added to pH 12. Acetic acid was added to pH B 4–5 and the product was collected by filtration and washed with water. Recrystallisation from methanol yielded (RS)-2-(n-undecyl)indoline-4-carboxylic acid (19.1 g) in the form of a buff solid, m.p. 105°–108° C.

EXAMPLE 133

Compound CRR

A solution of hydrogen chloride in ethanol (37% w/v, 20 ml) was added to a solution of (RS)-2-(n-undecyl)indoline-4-carboxylic acid (15.0 g) in ethanol (80 ml) and acetone (170 ml). After 30 seconds, anhydrous diethyl ether (800 ml) was added and the product was collected and washed with fresh anhydrous diethyl ether to give (RS)-2-(n-undecyl)indoline-4-carboxylic acid hydrochloride (14.2 g) in the form of a white powder, m.p. 220°–230° C. (with decomposition).

EXAMPLE 134

Compound CSS

A mixture containing 2-(n-eicosyl)indole-5-carboxylic acid (12.8 g), 5% w/w palladium on charcoal (2.0 g), 72% w/v aqueous perchloric acid (10 ml) and glacial acetic acid (150 ml) was heated by steam whilst shaken under hydrogen. Afterwards the mixture was filtered hot through diatomaceous earth, the residue was washed with hot glacial acetic acid (400 ml), and the combined filtrates were concentrated in vacuo to about 100 ml. The residue was poured into a mixture of ice and water, 50% w/v aqueous sodium hydroxide was added to pH 12 and acetic acid was then added to pH 4–5. The product was collected and recrystallised from methanol to give (RS)-2-(n-eicosyl)indoline-5-carboxylic acid hemimethanolate (4.8 g) as a pale brown solid. m.p. 110°–115° C.

EXAMPLE 135

Compound CTT

A mixture containing methyl 3-formyl-2-(n-heptyl)indole-6-crboxylate (64.5 g), palladium on charcoal (5% w/w, 12.4 g), 72% w/v aqueous perchloric acid (45 ml), and glacial acetic acid (450 ml) was externally heated with steam and shaken under an atmosphere of hydrogen. When the required hydrogen uptake had occurred, the mixture was filtered through diatomaceous earth, the residue was washed with hot glacial acetic acid (400 ml), and the filtrate was concentrated in vacuo to about 200 ml. The residue was poured into water (200 ml), ethanol (400 ml) was added, followed by a solution of sodium hydroxide (140 g) in water (400 ml), and the mixture was refluxed for 2.5 hours. The hot solution was poured into water (2 liters) and acidified to pH 4–5 with acetic acid. The solid product was recrystallised from acetonitrile to yield 2(RS),3(RS)-2-(n-heptyl)-3-methylindoline-6carboxylic acid (32.5 g) in the form of off-white crystals, m.p. 121°–124° C.

Methyl 3-formyl-2-(n-heptyl)indole-6-carboxylate, used as starting material, was prepared as follows:

A solution of phosphorus oxychloride (35 ml) in dimethylformamide (150 ml) was added to a solution of methyl 2-(n-heptyl)indole-6-carboxylate (67.5 g) in dimethylformamide (250 ml) and the resulting solution was stirred at between 70° and 85° C. for 2 hours. The mixture was then stirred for 30 minutes while the temperature dropped to 50° C. and was then poured into water (2 liters). Ice was added to reduce the temperature to 25° C. and a 50% w/v aqueous sodium hydroxide solution was added until the pH reached 11. After stirring for 10 minutes, acetic acid was added to pH 5 and the mixture was stirred until the product has solidified. Recrystallisation from methanol yielded methyl 3-formyl-2-(n-heptyl)indole-6-carboxylate (65.0 g) in the form of colourless, lustrous needles, m.p. 177°–180° C.

EXAMPLE 136

Compound CUU

By proceeding in a similar manner to that hereinbefore described in Example 1 for the preparation of 2-(n-pentadecyl)indole-6-carboxylic acid but replacing 3-(n-hexadecanamido)-4-methylbenzoic acid by (RS)-3-(2-ethylundecanamido)-4-methylbenzoic acid, there was prepared (RS)-2-(1-ethyldecyl)indole-6-carboxylic acid, in the form of an off-white solid, m.p. 70°–73° C. after chromatography of the oil obtained.

The 3-(2-ethylundecanamido)-4-methylbenzoic acid used as starting material was prepared as follows:

A mixture of (RS)-2-ethylundecanoyl chloride (1.16 g) and 3-amino-4-methylbenzoic acid (0.75 g) was placed in an oil bath at 90° C. and the temperature was gradually raised to 140° C. for 2 hours. After cooling, the solid was recrystallised from a mixture of ethanol (25 ml) and water (1 ml) to yield (RS)-3-(2-ethylundecanamido)-4-methylbenzoic acid (1.65 g) in the form of a white solid, m.p. 217°–220° C.

EXAMPLE 137

Compound CVV

A mixture of sodium 2-(n-undecyl)indole-6-carboxylate (5.0 g) and 3-chloro-1,2-propanediol (1.64 g) in diglyme (50 ml) was refluxed for 30 minutes. Potassium iodide (2.5 g) was added and the mixture refluxed for 48 hours. The mixture was cooled, water (50 ml) was added and the resulting emulsion was extracted with dichloromethane (2×100 ml). The combined extracts were dried over anhydrous magnesium sulphate, filtered, and the solvent evaporated to dryness. The solid residue was recrystallised from cyclohexane, filtered off and dried to give (RS)-2,3-dihydroxyprop-1-yl 2-(n-undecyl)indole-6-carboxylate (1.5 g) in the form of a white solid, m.p. 110°–112° C.

The following Example illustrates the preparation of the compounds of general formula XXI some of which are compounds of general formula I and others are intermediates in the preparation of other compounds of general formula I.

EXAMPLE 138

Compound of formula XXI

A suspension of 1-(4-carboxy-2-nitrophenyl)-2-nitropropene (14.78 g), palladium on charcoal catalyst (2.2 g; 5% w/w) and diatomaceous earth (3 g) in ethyl acetate (275 ml) containing glacial acetic acid (3.12 g) was shaken under an atmosphere of hydrogen at room temperature for 3 hours. The temperature of the reaction mixture rose slightly during this period. When hydrogen uptake was complete (96% of theory), the mixture was filtered through diatomaceous earth to remove the catalyst and the filtrate was washed with water (100 ml) and dried over magnesium sulphate. The ethyl acetate solution was concentrated in vacuo to give a pale yellow solid (7.36 g). The solid was dissolved in hot glacial acetic acid (100 ml) and water was added until a slight clouding occurred. The hot solution was treated with charcoal and then filtered. The resulting filtrate was cooled and the pale yellow solid which appeared was filtered off to give 2-methylindole-6-carboxylic acid (3.3 g), m.p. 200°–202° C. (with decomposition).

The 1-(4-carboxy-2-nitrophenyl)-2-nitropropene, used as starting material above, was prepared as follows:

Fuming nitric acid (95–98% w/w, 3.7 ml) was added dropwise with stirring to concentrated sulphuric acid (98% w/w, 30 ml), whilst maintaining the temperature at 0°–10° C. 1-(4-Carboxyphenyl)-2-nitropropene (15.3 g) was then added in portions with vigorous stirring over 15 minutes, whilst maintaining the temperature at 0°–10° C. The mixture was stirred for 30 minutes at the same temperature. The viscous reaction mixture was poured onto an ice/water mixture (600 ml) and the resulting yellow solid was filtered off and washed with water to give 1-(4-carboxy-2-nitrophenyl)-2-nitropropene (17.17 g), m.p. 200°–202° C. (with decomposition).

The 1-(4-carboxyphenyl)-2-niotropropene, used as starting material above, was prepared as follows:

A solution of 4-carboxybenzaldehyde (38.44 g) in nitroethane (360 ml) and butylamine (2 ml) was heated at reflux for 2 hours with azeotropic distillation of water using a Dean and Stark apparatus The solution was cooled to room temperature and the resulting solid was collected and recrystallised from isopropanol (250 ml) with hot filtration to give 1-(4-carboxyphenyl)-2-nitropropene (31.57 g) in the form of a yellow crystalline solid, m.p. 212°–214° C.

Compounds of general formula I may be prepared in a similar manner to that described above but replacing 1-(4-carboxy-2-nitrophenyl)-2-nitropropene by the appropriate 1-(carboxy-2-nitrophenyl)-2-nitroalkene.

The present invention includes within its scope pharmaceutical compositions which comprise at least one of the compounds of general formula I or a pharmaceutically acceptable salt thereof in association with a pharmaceutically acceptable carrier or coating. In clinical practice the compounds of the present invention may be administered parenterally, but are preferably administered rectally or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing one or more of the compounds of formula I or a pharmaceutically acceptable salt thereof.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally between 0.1 and 50 mg/kg body weight per day by oral administration. For example, as hypolipidaemic agents and in associated cardiovascular diseases between 10 and 50 mg/kg body weight per day by oral administration, and in the treatment of diabetes between 5 and 40 mg/kg body weight per day by oral administration.

The following Example illustrates pharmaceutical compositions according to the present invention.

EXAMPLE 139

No. 2 size gelatin capsules each containing:

| | |
|---|---|
| 2-(n-pentadecyl)indole-6-carboxylic acid | 20 mg |
| lactose | 100 mg |
| starch | 60 mg |
| dextrin | 40 mg |
| magnesium stearate | 1 mg | were prepared in accordance with the usual procedure.

We claim:

1. Indole and indoline compound of the formula:

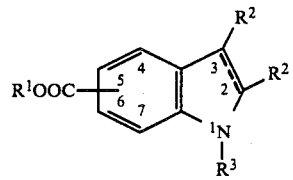

wherein ==== indicates a double bond or a single bond between carbon atoms, $R^1$ represents hydrogen or alkyl of 1 through 6 carbon atoms and one of the symbols $R^2$ represents alkyl of 9 through 24 carbon atoms and the other symbol $R^2$ represents alkyl of 1 through 24 carbon atoms or hydrogen, and $R^3$ represents alkyl of 1 through 6 carbon atoms or hydrogen, and pharmaceutically acceptable salts thereof.

2. Compounds according to claim 1 wherein the group $R^1OOC—$ is attached to the 5 or 6 position of the indole or indoline ring system.

3. Compounds according to claim 1 wherein $R^1$ represents hydrogen.

4. Compounds according to claim 1, wherein one of the symbols $R^2$ represents alkyl of 9 through 20 carbon atoms, and the other symbol $R^2$ represents alkyl of 1 through 24 carbon atoms or hydrogen.

5. Compounds according to claim 1 wherein the second symbol $R^2$ represents hydrogen.

6. Compounds according to claim 4 wherein the second symbol $R^2$ represents alkyl of 1 through 6 carbon atoms.

7. Compounds according to claim 1 wherein one of the symbols $R^2$ represents hydrogen or alkyl of 1 through 5 carbon atoms, and that particular symbol is attached to the 3 position of the indole or indoline ring system.

8. Compounds according to claim 7 wherein the symbol $R^2$ attached to the 3 position of the indole or indoline ring system represents methyl.

9. Compounds according to claim 1, wherein $R^1$ represents methyl, ethyl, butyl, 2,3-dihydroxyprop-1-yl, allyl or pivaloyloxymethyl.

10. Compounds according to claim 1 wherein the symbol $R^3$ in the formula depicted in claim 1 represents hydrogen.

11. Indole and indoline compound according to claim 1 of the formula:

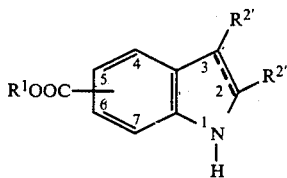

wherein ==== indicates a double bond or a single bond between carbon atoms, the group $R^1OOC-$ is attached to the 5 or 6 position of the indole or indoline ring system, $R^1$ represents alkyl of 1 through 6 carbon atoms or hydrogen, and one of the symbols $R^{2'}$ represents alkyl of 9 through 24 carbon atoms and the other symbol $R^{2'}$ represents alkyl of 1 through 24 carbon atoms, and pharmaceutically acceptable salts thereof.

12. Compounds according to claim 11 wherein $R^1$ represents hydrogen.

13. Compounds according to claim 11 wherein one of the symbols $R^{2'}$ represents alkyl of 9 through 20 carbon atoms, and the other symbol $R^{2'}$ represents alkyl of 1 through 24 carbon atoms.

14. Compounds according to claim 11, wherein the second symbol $R^{2'}$ represents alkyl, of 1 through 5 carbon atoms and that particular symbol is attached to the 3 position of the indole or indoline ring system.

15. Indole and indoline compound according to claim 1 of the formula:

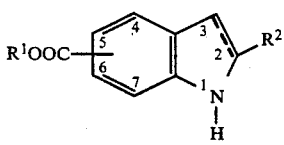

wherein ==== indicates a double bond or a single bond between carbon atoms, the group $R^1OOC-$ is attached to the 5 or 6 position of the indole or indoline ring system, $R^1$ represents alkyl of 1 through 6 carbon atoms or hydrogen, and $R^2$ represents alkyl of 9 through 24 carbon atoms, and pharmaceutically acceptable salts thereof.

16. Compounds according to claim 15 wherein $R^1$ represents hydrogen.

17. Compounds according to claim 15 wherein $R^2$ represents alkyl or 9 through 20 carbon atoms.

18. Compound according to claim 11, wherein $R^1$ represents methyl, ethyl or butyl.

19. 2-(n-Octadecyl)indole-5-carboxylic acid and pharmaceutically acceptable salts thereof.

20. 2-(n-Undecyl)indole-6-carboxylic acid and pharmaceutically acceptable salts thereof.

21. 2-(n-Pentadecyl)indole-5-carboxylic acid and pharmaceutically acceptable salts thereof.

22. 2-(n-Undecyl)indole-5-carboxylic acid and pharmaceutically acceptable salts thereof.

23. 2-(n-Pentadecyl)indole-6-carboxylic acid and pharmaceutically acceptable salts thereof.

24. 2-(1-Methyldecyl)indole-6-carboxylic acid and pharmaceutically acceptable salts thereof.

25. 2-(n-Undecyl)indoline-5-carboxylic acid and pharmaceutically acceptable salts thereof.

26. 2-(n-Decyl)indoline-5-carboxylic acid and pharmaceutically acceptable salts thereof.

27. 2-(n-Undecyl)indoline-6-carboxylic acid and pharmaceutically acceptable salts thereof.

28. 2-(n-Undecyl)-3-methylindoline-6-carboxylic acid and pharmaceutically acceptable salts thereof.

29. 2-n-Heptadecylindole-5-carboxylic acid.

30. 2-n-Dodecylindole-6-carboxylic acid.

31. 2-n-Hexadecylindole-5-carboxylic acid.

32. Indole and indoline compound of the formula:

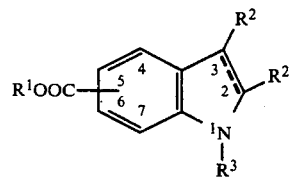

wherein ==== indicates a double bond or a single bond between carbon atoms, $R^1$ represents alkyl of 1 through 6 carbon atoms substituted by one or more than one of the same type of substituents selected from the hydroxy group, alkenyl groups of 2 through 5 carbon atoms, and alkanoyloxy groups of 2 through 7 carbon atoms, and one of the symbols $R^2$ represents alkyl of 7 through 24 carbon atoms and the other symbol $R^2$ represents alkyl of 1 through 24 carbon atoms or hydrogen, and $R^3$ represents alkyl of 1 through 6 carbon atoms or hydrogen, and pharmaceutically acceptable salts thereof.

33. Compounds according to claim 32 wherein $R^1$ represents 2,3-dihydroxyprop-1-yl, allyl or pivaloyloxymethyl.

34. A pharmaceutical composition useful as a hypolipidaemic agent which comprises, as active ingredient, an effective amount of an indole or indoline compound of the formula:

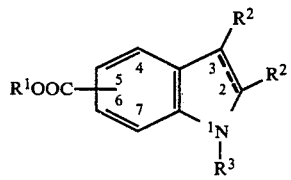

wherein ==== indicates a double bond or a single bond between carbon atoms, $R^1$ represents hydrogen, alkyl of 1 through 6 carbon atoms, or alkyl of 1 through 6 carbon atoms substituted by one or more than one of the same type of substituents selected from the hydroxy group, alkenyl groups of 2 through 5 carbon atoms, and alkanoyloxy groups of 2 through 7 carbon atoms, and one of the symbols $R^2$ represents alkyl of 7 through 24 carbon atoms and the other symbol $R^2$ represents alkyl of 1 through 24 carbon atoms or hydrogen, and $R^3$ represents alkyl of 1 through 6 carbon atoms or hydrogen, or a pharmaceutically acceptable salt thereof, in association with a pharmaceutically acceptable carrier.

* * * * *

UNITED STATES PATENT AND TRADEMARK OFFICE
CERTIFICATE OF CORRECTION

PATENT NO. : 4,493,843
DATED : January 15, 1985
INVENTOR(S) : Michael J. Ashton et al.

It is certified that error appears in the above-identified patent and that said Letters Patent is hereby corrected as shown below:

Column 57, claim 9 should read:

-- 9. Compounds according to claim 1, wherein $R^1$ represents methyl, ethyl or butyl. --

Signed and Sealed this

Twenty-eighth Day of May 1985

[SEAL]

Attest:

DONALD J. QUIGG

Attesting Officer  Acting Commissioner of Patents and Trademarks